United States Patent [19]

Matier et al.

[11] 4,096,183

[45] Jun. 20, 1978

[54] STYRYLSULFONYLAMIDINES

[75] Inventors: William L. Matier; William T. Comer, both of Evansville, Ind.

[73] Assignee: Mead Johnson & Company, Evansville, Ind.

[21] Appl. No.: 825,996

[22] Filed: Aug. 19, 1977

Related U.S. Application Data

[60] Division of Ser. No. 601,563, Aug. 4, 1975, Pat. No. 4,052,455, which is a continuation-in-part of Ser. No. 459,152, Apr. 8, 1974, abandoned, which is a continuation-in-part of Ser. No. 368,547, Jun. 11, 1973, abandoned.

[51] Int. Cl.² ............... C07C 143/38; C07C 143/40; C07C 123/00
[52] U.S. Cl. .................................. 260/556 AR; 544/8
[58] Field of Search ............... 260/564 R, 556 AR

[56] References Cited

FOREIGN PATENT DOCUMENTS 2,024,299  12/1970  Germany ..................... 260/564

*Primary Examiner*—Gerald A. Schwartz
*Attorney, Agent, or Firm*—Robert H. Uloth; Robert E. Carnahan

[57] ABSTRACT

Styrylamidines are prepared by treating styrylsulfonylamidines with base. The styrylamidines are effective in the prevention of aggregation of blood platelets and as analgesics. Compounds of the invention are also useful as anticonvulsants, diuretics and antihypertensive agents. The styrylsulfonylamidines of the invention which serve as precursors to the styrylamidines also have analgesic properties. Illustrative of the styrylamidines of the present invention are 4-amino-N-(4-aminostyryl)benzamidine and N-(3,4-dichlorostyryl)acetamidine. An example of a styrylsulfonylamidine is N-(styrylsulfonyl)acetamidine.

39 Claims, No Drawings

STYRYLSULFONYLAMIDINES

CROSS REFERENCE TO RELATED APPLICATION

This application is a divisional of continuation-in-part application Ser. No. 601,563 filed Aug. 4, 1975 (and now U.S. Pat. No. 4,052,455) of then co-pending U.S. patent application Serial No. 459,152 filed Apr. 8, 1974 (now abandoned), which is a continuation-in-part application of U.S. patent application Ser. No. 368,547 filed June 11, 1973 (now abandoned).

BACKGROUND OF THE INVENTION

This invention is broadly concerned with amidines having drug and bio-affecting properties. More particularly, the invention relates to styrylamidines, to styrylsulfonylamidine intermediates therefor and a process for the preparation of styrylamidines. The styrylamidines inhibit aggregation of blood platelets and also possess analgesic activity. The styrylamidines, particularly those having aromatic halogen substituents such as N-(2,6-dichlorostyryl)acetamidine are also useful as anticonvulsant, hypotensive and antihypertensive agents. Apart from being precursors to the styrylamidines, the styrylsulfonylamidines of the invention have analgesic activity.

With respect to prior art amidines, the styrylsulfonylamidines and the styrylamidines of this invention are distinct and novel. The following publications are cited by way of illustrating the closest prior art known to the inventors.

A. Marxer, Helvetica Chimica Acta, 55, 430 (1972) describes a new synthesis of benzamidines substituted at the imide nitrogen by a 1,2-diphenyl-vinyl group. None of the amidines of the instant invention which have a styryl or styrylsulfonyl radical at that position are described.

B. G. Advani, et al., Tetrahedron Letters No. 56, 5825-5828 (1968) described N-$\beta$-styrylamidines having pyrrolidino or morpholino groups in place of the $NH_2$ moiety of the amidino group whereas the amidines of the present invention do not.

K. Hasegawa and S. Hirooka, Bulletin Chemical Society of Japan, 45, 1893-1896 (1972) discloses S-methylthioureas containing phenylethene-1-sulfonyl substituents useful in the synthesis of 1,2,4-thiadiazine-1,1-dioxides. The styrylsulfonylamidines and styrylamidines of the instant invention are not disclosed and are structurally unrelated in that they are classified as amidines rather than "S-methylthioureas".

French Pat. No. 2,036,528 teaches that certain "ethenesulfonamides" are useful as intermediates in the preparation of dioxothiadiazines. "Ethenesulfonamides" wherein the amidino nitrogen is part of a nitrogen heterocycle are specifically disclosed.

A group of cinnamylamidines exemplified by N-(4-chlorocinnamyl)acetamidine is described in U.S. Pat. No. 3,413,345 as reportedly possessing hypotensive effects which are quick in onset and of considerable duration. While formally related, the cinnamylamidines of U.S. Pat. No. 3,413,345 differ from the styrylamidines of the instant invention in that the former are non-conjugated amidines whereas the latter have a conjugated amidine system resulting in marked chemical differences.

SUMMARY OF THE INVENTION

This invention is concerned with a group of styrylamidines, a process for the preparation thereof, and a method of producing an analgesic and antithrombogenic effect comprising administration of such compounds. Compounds of the invention also have anticonvulsant, diuretic and hypotensive effects when systemically administered to mammals. More particularly, the invention pertains to styrylamidines of Formula I and non-toxic pharmaceutically acceptable acid addition salts thereof.

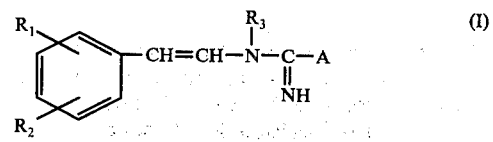

The substances represented by Formula I are novel compositions of matter and are effective as central nervous system analgesics and as inhibitors of blood platelet aggregation in mammals.

In the above formula, the symbols "$R_1$, $R_2$, $R_3$ and A" have the following meanings:

$R_1$ represents a member of the group consisting of hydrogen, lower alkyl containing 1 to 4 carbon atoms inclusive, nitro, amino, halogen, cyclohexyl, carbamoyl, lower alkylsulfonyl, sulfamoyl, and lower alkanoylamido. $R_2$ represents hydrogen or halogen with the proviso that when $R_1$ is halogen, $R_2$ can represent up to two additional halogen. $R_3$ is hydrogen, cyclopropyl or lower alkyl of 1 to 4 carbon atoms inclusive.

The symbol "A" represents a member of the group consisting of lower alkyl of from 1 to 8 carbon atoms inclusive, di(lower)alkylaminophenyl, phenyl, benzyl, $\beta$-naphthyl, styryl, phenylbutadienyl, cycloalkyl of 3 to 6 carbon atoms inclusive, or a $(X)_n$-phenyl radical which is represented by the symbol

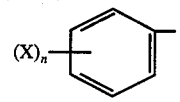

wherein X signifies a member of the group consisting of lower alkoxy, halogen, nitro, amino, lower alkanoylamido, and $n$ signifies an integer of 1 or 2.

It is to be understood that by employment of the terms "lower alkyl", "lower alkoxy" and "lower alkanoylamido" herein, it is meant that the carbon chains of each group include both straight and branched carbon radicals of the designated number of carbon atoms. Exemplary of carbon chain radicals containing 1 to 8 carbon atoms are methyl, ethyl, propyl, isopropyl, 1-butyl, 1-methylpropyl, 2-methylpropyl, hexyl, tert.-butyl and the like. The term "lower alkanoylamido of from 2 to 4 carbon atoms inclusive" comprehends both straight and branced chain carbon radicals wherein the total number of carbon atoms includes the carbonyl divalent radical. By the term "halogen" as used herein, it is meant to connote all members of that group, i.e., chlorine, bromine, fluorine, and iodine. Examples of "cycloalkyl" are cyclopropyl, cyclobutyl, cyclopentyl and cyclohexyl.

Those skilled in the art will recognize that the subject styrylamidines of Formula I and their salts wherein $R_3$ is hydrogen can exist in more than one tautomeric modification as depicted by Formulas II and III wherein $R_1$, $R_2$ and A have the meaning previously defined.

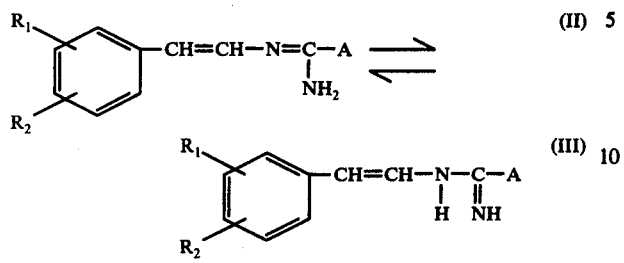

Without being bound by any theory, it is believed that the protonated styrylamidines of the present invention, as in the case with the acid addition salts, are best represented by a delocalized double bond illustrated by Formula IV

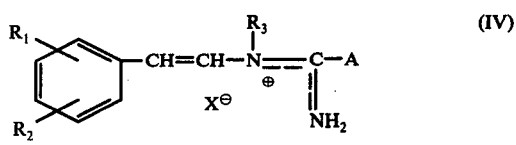

wherein $X^\ominus$ symbolizes an anion rather than fixed double bonds shown in the foregoing tautomeric forms.

It will also be recognized that compounds of Formula I exist as cis or trans geometrical isomers as the result of different arrangements of groups around the ethylenic double bond. According to nuclear magnetic resonance studies, the compounds of Formula I are believed to have the trans-configuration on the basis of vinyl proton coupling constants.

The compounds of this invention characterized by Formula I are obtained by a method which comprises treating a styrylsulfonylamidine of Formula

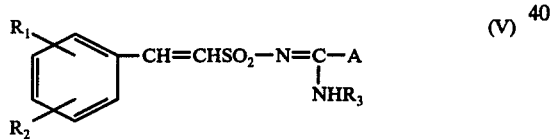

wherein $R_1$, $R_2$, $R_3$ and A are as herein defined with one equivalent of an alkali base such as sodium hydroxide, potassium hydroxide and the like, in a reaction-inert solvent whereby $SO_2$ is eliminated and thereafter, if desired, reacting the resulting product in free base form with an acid to form an acid addition salt thereof.

An alternate method of providing compounds of Formula I wherein $R_2$ is amino involves reducing the corresponding nitro substituted styrylamidine. Reduction of nitrostyrylamidines of Formula I to the corresponding amino compounds is accomplished by selective reduction with sodium borohydride in the presence of 10% palladium on carbon catalyst according to the method of R. Neilson, et al., J. Chem. Soc., 371, (1962).

Compounds of Formula I containing lower alkanoylamido radicals can also be obtained by acylating the corresponding amino substituted styrylamidine with a lower alkanoyl halide or anhydride.

By reaction-inert solvent is meant a solvent wherein the reactants are soluble and does not interfere with their interaction. In this respect, acetone and dimethylsulfoxide are particularly preferred. When acetone is selected as the reaction solvent, 2 to 10 moles of base per mole of styrylsulfonylamidine is preferably employed with a reaction period of from about 1 to 3 hr. at a temperature of about 25° C. When dimethylsulfoxide is selected as the reaction solvent, an equi-molar ratio of base to the styrylsulfonylamidine is employed with a longer reaction period of from 24 to preferably 64 hours. Styrylsulfonylamidines containing electron withdrawing $R_1$ or $R_2$ substituents provide higher yields of the corresponding styrylamidine product compared to yields of styrylsulfonylamidines wherein $R_1$ and $R_2$ are hydrogen.

The compounds characterized by Formula I have basic properties and are converted to corresponding non-toxic pharmaceutically acceptable acid addition salts by admixture of the base with a selected acid in an inert organic solvent such as ethanol, benzene, ethyl acetate, ether, halogenated hydrocarbons (e.g., dichloroethane), and the like. A preferred method of salt preparation is to treat the base with substantially one chemical equivalent of an acid such as hydrogen chloride or isethionic acid in ethanol solution. The salt is isolated from the ethanolic solution by chilling or the addition of an appropriate co-solvent such as ether. Both the free base and salt forms of the products of Formula I are useful for the purpose of the invention although salts are particularly preferred because of their increased water solubility. It is to be understood that the term "pharmaceutically acceptable acid addition salts" as used herein is construed to mean a combination of the compounds of the present invention with a relatively non-toxic inorganic or organic acid, the anion of which is pharmaceutically ineffective in the usual dosage. Some examples of inorganic or organic acids which may be employed to provide a non-toxic pharmaceutically acceptable acid addition salt of the compounds of Formula I are: sulfuric, phosphoric, hydrochloric, hydrobromic, hydroiodic, sulfamic, acetic, lactic, maleic, succinic, malic, fumaric, tartaric, citric, gluconic, glutaric, ascorbic, benzoic, cinnamic, isethionic, and related acids.

The styrylsulfonylamidine precursors of the compounds of the present invention characterized by Formula I are obtained by reacting a styrylsulfonyl chloride of the formula

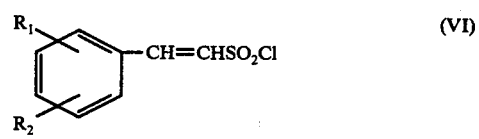

wherein $R_1$ and $R_2$ are as herein defined by excluding amino with an amidine of the formula

wherein A is as herein defined to yield the new styrylsulfonylamidines illustrated by general Formula V.

An alternate procedure for preparing styrylsulfonylamidines of Formula V comprises reacting a N-styrylsulfonylimidoyl chloride of Formula VIII

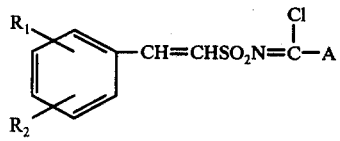

(VIII)

with an $R_3NH_2$ amine wherein $R_1$, $R_2$, $R_3$, and A are as herein defined.

Styrene intermediates employed in the preparation of styrylsulfonyl chlorides of Formula VI are obtained from the corresponding benzaldehydes by the procedures of L. A. Brooks, J. Amer. Chem. Soc., 66, 1295 (1944). Conversion of the styrene intermediates to styrylsulfonyl chlorides is carried out by methods of F. G. Bordwell, et al., J. Amer. Chem. Soc., 68, 139, 1778 (1946) and B. M. Culbertson, et al., J. Chem. Soc. (c) 992 (1968).

Illustrative of styrylsulfonyl chlorides of Formula VI which are useful in the preparation of the styrylsulfonylamidine precursors of Formula V of the present invention are:

styrylsulfonyl chloride,
4-chlorostyrylsulfonyl chloride,
3,4-dichlorostyrylsulfonyl chloride,
2-nitrostyrylsulfonyl chloride,
4-nitrostyrylsulfonyl chloride,
4-carbamoylstyrylsulfonyl chloride,
4-sulfamoylstyrylsulfonyl chloride,
4-(methanesulfonyl)styrylsulfonyl chloride,
4-cyclohexylstyrylsulfonyl chloride,
3-bromo-4-cyclohexylstyrylsulfonyl chloride,
4-acetamidostyrylsulfonyl chloride,
2-fluorostyrylsulfonyl chloride,
2,5-dichlorostyrylsulfonyl chloride,
4-(2-methylpropionamido)styrylsulfonyl chloride,
2,6-dichlorostyrylsulfonyl chloride,
2-chloro-6-methylstyrylsulfonyl chloride,
2,3,6-trichlorostyrylsulfonyl chloride.

The amidine intermediates of Formula VII are generally known compounds which are available from commercial sources or are conveniently prepared according to the methods of L. Weintraub, et al., J. Org. Chem., 33, 1679 (1968) and P. Oxley, et al. J. Chem. Soc., 147 (1946), 303 (1948).

Illustrative of suitable amidine intermediates of Formula VII which reacted with the styrylsulfonyl chlorides of Formula VI provide styrylsulfonylamidines of Formula V are:

4-nitrobenzamidine,
acetamidine,
benzamidine,
phenylacetamidine,
4-nitrobenzamidine,
3-nitrobenzamidine,
4-aminobenzamidine,
3-aminobenzamidine,
2-nitrobenzamidine,
2-aminobenzamidine,
4-dimethylaminobenzamidine,
cinnamamidine,
beta-naphthamidine,
4-chlorobenzamidine,
3-acetamidobenzamidine,
3,4-dichlorobenzamidine,
4-styrylbenzamidine,
4-phenylbutadienylbenzamidine,
4-(dibutylamino)benzamidine,
2-methylpropionamidine.

The compounds of this invention characterized by Formula I are therapeutically active substances which posses antithrombogenic and analgesic activities when present in an effective amount in the mammalian circulatory system.

Measurement of the antithrombogenic activity of the compounds of Formula I is carried out by standard pharmacological tests essentially described by Born, Nature, 194, 927 (1962) and O'Brien, J. Clin. Path., 15, 446 (1962). This test comprises a nephelometric method in which the change in turbidity of a specimen of platelet rich plasma (human or rabbit) is measured on causation of platelet aggregation by addition of a thrombogenic inducing agent such as adenosine diphosphate or collagen. The compounds of the present invention are effective antithrombogenic agents according to this test at concentrations in the order of about 0.5 to 90 mcg./0.5 ml. platelet rich plasma. In the intact animal, the antithrombogenic effect is readily observed by applying the above test to blood samples withdrawn prior to and after administration of a compound of the present invention. While compounds of Formula I generally exhibit significant antithrombogenic activity, compounds which reduce the thrombogenic capacity of collagen or adenosine diphosphate induced platelet aggregation by 50% or more at concentrations of less than 15 mcg./0.5 ml. of platelet rich plasma are preferred and by way of example there can be mentioned:

N-styrylbenzamidine hydrochloride,
N-(3,4-dichlorostyryl)acetamidine hydrochloride,
3,5-diamino-N-(4-nitrosytryl)benzamidine trichydrochloride,
4-amino-N-(4-nitrostyryl)benzamidine hydrochloride,
4-(dimethylamino)-N-(4-nitrostyryl)benzamidine isethionate,
N-(4-aminostyryl)benzamidine dihydrochloride,
N-(2-aminostyryl)benzamidine dihydrochloride,
4-amino-N-(4-aminostyryl)benzamidine trihydrochloride,
3-amino-N-(4-aminostyryl)benzamidine trihydrochloride,
N-(4-acetamidostyryl)benzamidine hydrochloride,
N-(3-bromo-4-cyclohexylstyryl)acetamidine hydrochloride,
N-(3,4-dichlorostyryl)cyclopropanecarboxamidine.

A particularly preferred group of styrylamidines of Formula I comprises styrylbenzamidines wherein $R_1$ and $R_2$ are hydrophilic substitutents such as sulfamoyl, carbamoyl, amino, and the like, and the X substitutent is a radical whose electrons are capable of being delocalized such as dialkylamino, amino, nitro, styryl, phenylbutadienyl, and the like.

Another preferred group of styrylamidines of Formula I comprises styrylalkylamidines wherein $R_1$ and $R_2$ are lipophilic substitutents such as alkyl, cycloalkyl, halogen, and the like.

A still further preferred group of compounds comprises Formula I styrylamidines wherein A is methyl, $R_1$ and $R_2$ are halogen and $R_3$ is hydrogen or methyl.

Apart from the antithrombogenic activity, the compounds of the present invention of Formula I have central nervous system analgesic activity as demonstrated by prevention of the phenylquionone writhing syndrome in mice. In this test, groups of 10-20 mice are injected subcutaneously or orally with different doses of the test compound. At predetermined time intervals, the mice receive 2.5 mg./kg. phenylquinone intraperitoneally. The total number of writhing episodes is counted for each mouse for 10 min. and the average percent decrease in writhing recorded for each dose.

The novel styrylsulfonylamidines of Formula V in addition to being useful as precursors to the styrylamidine products of Formula I have analgesic utility as measured in the foregoing phenylquinone writhing test. A preferred class of styrylsulfonylamidines of Formula V having particularly significant analgesic activity are those wherein $R_1$ and $R_2$ are each hydrogen, nitro or halogen and A is phenyl or lower alkyl of from 1 to 8 carbon atoms inclusive. Analgesic activity at the time interval indicated following administration of compounds representative of this class are given in Table I below.

TABLE I.

ANALGESIC ACTIVITY OF STYRYLSULFONYL-AMIDINES

| Name | Percent Inhibition | | Time Interval |
|---|---|---|---|
| | Subcutaneous (6 mg./kg.) | Oral (100 mg./kg.) | |
| N-(styrylsulfonyl)acetamidine | 38 | — | 15 min. |
| N-(4-nitrostyrylsulfonyl)-acetamidine | 36 | — | 60 min. |
| N-[(3,4-dichlorostyryl)sulfonyl]-acetamidine | 28 | — | 30 min. |
| N-[(3,4-dichlorostyryl)sulfonyl]-acetamidine | — | 36 | 120 min. |
| N-(styrylsulfonyl)benzamidine | 36 | — | 30 min. |
| N-(styrylsulfonyl)benzamidine | — | 26 | 60 min. |

According to the present invention, the antithrombogenic process is carried out in mammals by systemic administration of a non-toxic effective dose of the styrylamidines of Formula I ranging from about 0.01 to 100 mg./kg. of body weight of a mammal. By systemic administration it is intended to include both oral and parenteral routes. Examples of parenteral administration are intramuscular, intravenous, intraperitoneal and subcutaneous. As would be expected, the dosage will vary with the form of administration and particular compound chosen. In general, the process for preventing aggregation of blood platelets in a mammal having a thromboembolic condition comprises administration to said mammal an antithrombogenic effective dose of a compound of Formula I or a pharmaceutically acceptable salt thereof to provide a blood level of from 0.5 to 90 micrograms of said compound per 0.5 milliliter blood.

It is to be understood that the term "non-toxic effective dose" as used herein refers to quantity of active ingredient necessary to produce the desired therapeutic effect without causing any harmful or deleterious side effects.

Aside from antithrombogenic and analgesic effects, compounds of Formula I wherein $R_1$ and $R_2$ substituents are halogen (particularly chlorine), $R_3$ is hydrogen or methyl and A is selected from the group consisting of lower alkyl of from 1 to 8 carbon atoms inclusive or cycloalkyl of from 3 to 6 carbon atoms inclusive, are useful as anticonvulsant, hypotensive and antihypertensive agents. In some instances, the compounds also exhibit diuretic activity. The aforesaid utilities can be demonstrated by standard pharmacological test procedures. For example, N-(2,6-dichlorostyryl)acetamidine in the mouse electroshock test of E. A. Swinyard, J. Amer. Pharm. Associations, Sci, Ed., 38, 201 (1949) has an oral $ED_{50}$ of 44 mg./kg. body weight. In contrast, the prior art cinnamylamidine, N-(4-chlorocinnamyl)acetamidine is completely inactive at a dose of 250 mg./kg. body weight.

In the anesthetized normotensive dog, intravenous administration of N-(2,6-dichlorostyryl)acetamidine in a dosage range of from 0.01 to 10 mg./kg. body weight provides a dose related reduction in blood pressure. For instance, of 1.0 mg./kg. body weight, this compound provides a 33% reduction in blood pressure while at 10.0 mg./kg. body weight, a 64% reduction in blood pressure is obtained. In the same test procedure, the prior art cinnamylamidine, N-(4-chlorocinnamyl)acetamidine, provided a 12% increase in blood pressure with a 6% decrease in heart rate at a dose of 1.0 mg./kg. body weight. At a dose of 10.0 mg./kg. body weight, the prior art cinnamylamidine provides an increase of 26% in blood pressure. In the spontaneous hypertensive rat, oral administration of N-(2,6-dichlorostyryl)acetamidine at a dose of 5 to 50.0 mg./kg. body weight provides a substantial reduction of blood pressure whereas, at 50 mg./kg. body weight, the prior art cinnamylamidine "N-(4-chlorocinnamyl)acetamidine" is devoid of antihypertensive effects and in fact affords a slight increase in blood pressure at that dose.

Compounds particularly preferred for their antihypertensive properties are:

N-(2,6-dichlorostyryl)acetamidine,
N-(2,6-dichlorostyryl)propionamidine,
N-(2,6-dichlorostyryl)cyclopropanecarboxamidine,
N-Methyl-N-(2,6-dichlorostyryl)acetamidine.

It is understood that a further embodiment of this invention includes a method of producing an antihypertensive effect comprising systemic administration to a mammal in need thereof a non-toxic effective dose of from about 0.01 to 100 mg./kg. body weight of said mammal to provide an antihypertensive effect of a compound selected from the group consisting of N-(2,6-dichlorostyryl)acetamidine, N-(2,6-dichlorostyryl)propionamidine, N-(2,6-dichlorostyryl)cyclopropanecarboxamidine and N-methyl-N-(2,6-dichlorostyryl)acetamidine.

N-(2,6-dichlorostyryl)acetamidine is orally effective as a diuretic agent according to the W. L. Lipschitz, et al., J. Pharmacol. Expt. Therap., 79, 97 (1943) test doubled the urine output at a dose of 12.5 mg./kg. body weight. In the same test, the prior art cinnamylamidine "N-(4-chlorocinnamyl)acetamidine" is essentially inactive at an oral dose of 30 mg./kg. body weight.

The styrylamidines of Formula I can be formulated according to conventional pharmaceutical practice to provide pharmaceutical composition of unit dosage form which may include solid preparations suitable for oral administration such as tablets, capsules, powders, granules, emulsions, suspensions, and the like. The solid preparation may comprise an inorganic carrier, e.g., talc, or an organic carrier such as lactose or starch. Additives such as magnesium stearate (a lubricant) can also be included. Liquid preparations suitable for parenteral administration include solutions, suspensions or emulsions of the compounds of Formula I in combination with the usual diluent such as water, petroleum jelly, and the like; a suspension media such as polyoxyethyleneglycol, vegetable oils and the like. The compositions may also contain other additional ingredients such as absorbing agents, stabilizing agents, and buffers.

The compounds which constitute this invention and their methods of preparation will appear more fully from a consideration of the following examples and appended claims which are given for the purpose of illustration only and are not to be construed as limiting the invention in spirit or in scope.

In regard to "NMR" data given below, chemical shift delta values are in parts per million and the following multiplicity notations employed: s=singlet, d=doublet, t=triplet, m=multiplet (center listed), bs=broad singlet, bd=broadened doublet (one J value listed), bm=very broad lines (either a multiplet or more than one singlet). Solvent and internal reference peak are also identified: TMS=tetramethylsilane, DSS=3-(trimethylsilyl)-1-propanesulfonic acid sodium salt.

EXAMPLE 1

N-(Styrylsulfonyl)benzamidine (4.3 g., 0.015 mole) is added portion-wise to a stirred mixture of 50% sodium hydroxide (1.2 g., 0.015 mole) in 25 ml. of dimethylsulfoxide. After stirring the mixture for 64 hr., at 25° C., the mixture is poured into 250 ml. of cold water and made strongly basic with 5% sodium hydroxide. The basified solution is extracted several times with ether, the ethereal extracts combined, washed with water, dried over potassium carbonate, and concentrated to provide the N-styrylbenzamidine free base as a yellow oily residue. The free base oil is taken up in ethanol, acidified with ethanolic hydrogen chloride and the hydrochloride salt isolated by dilution with ether. Trituration of the salt with acetone affords 0.25 g. (6.5% yield) of N-STYRYLBENZAMIDINE HYDROCHLORIDE, m.p. 226.5°–228.0° C. (corr.).

Analysis. Calcd. for $C_{15}H_{14}N_2 \cdot HCl$ (percent): C, 69.60; H, 5.84; N, 10.82. Found (percent): C, 69.34; H, 5.80; N, 10.79.

NMR (DMSO-$d_6$, TMS): 6.95d (14.0 Hz), 7.10m, 8.25bd (14.0 Hz), 10.33bs, 12.03bs.

EXAMPLE 2

N-(Styrylsulfonyl)acetamidine is treated with sodium hydroxide according to the procedure of Example 1. Isolation of the styrylamidine product is carried out by quenching the reaction mixture in water, acidifying the aqueous mixture with 3N hydrochloric acid and filtering. The filtrate is made basic with sodium hydroxide and extracted with chloroform. Concentration of the chloroform extract provides the N-(styryl)acetamidine free base as a gum. The free base is converted to the hydrochloride in acetone with ethanolic hydrogen chloride. Acetone trituration of the crude hydrochloride and crystallization from isopropyl alcohol affords a 3% analytical yield of N-(STYRYL)ACETAMIDINE HYDROCHLORIDE having a capillary melting point of 167.0°–183.0° C. when inserted in bath at 95° C.

Analysis. Calcd. for $C_{10}H_{12}N_2 \cdot HCl$ (percent): C, 61.05; H, 6.66; N, 14.24. Found (percent): C, 61.16; H, 6.76; N, 14.20.

NMR (DMSO-$d_6$, TMS): 2.33s, 6.65d (14.0 Hz), 7.38m, 8.00bd (14.0 Hz), 9.87bs, 11.88bs.

EXAMPLE 3.

N-(4-chlorostyrylsulfonyl)acetamidine treated with sodium hydroxide according to the procedure of Example 1 provides a 12% analytical yield of N-(4-CHLOROSTYRYL)ACETAMIDINE HYDROCHLORIDE, m.p. 228°–234.5° C. (corr.), from methanol-isopropyl ether.

Analysis. Calcd. for $C_{10}H_{11}ClN_2 \cdot HCl$ (percent): C, 51.96; H, 5.24; N, 12.13. Found (percent): C, 51.79; H, 5.27; N, 11.94.

NMR (DMSO-$d_6$, TMS): 2.38s, 6.66d (14.2 Hz), 7.57m, 8.10bd (14.2 Hz), 9.83bs, 11.88bs.

EXAMPLE 4

Treatment of N-(3,4-dichlorostyrylsulfonyl)acetamidine with sodium hydroxide according to the procedure of Example 1 affords N-(3,4-dichlorostyryl)acetamidine free base, m.p. 125°–128° C. Conversion of the free base to the hydrochloride salt with ethanolic hydrogen chloride in methanol provides N-(3,4-DICHLOROSTYRYL)ACETAMIDINE HYDROCHLORIDE, m.p. 215°–224° C. (dec.)(corr.), from methanol-acetone.

Analysis. Calcd. for $C_{10}H_{10}Cl_2N_2 \cdot HCl$ (percent): C, 45.22; H, 4.18; N, 10.55. Found (percent): C, 45.33; H, 4.39; N, 10.47.

NMR (DMSO-$d_6$, TMS): 2.31s, 6.48d (14.0 Hz), 7.51m, 7.82m, 7.99bd (14.0 Hz), 9.83bs, 11.67bs.

EXAMPLE 5

Treatment of N-(3,4-dichlorostyrylsulfonyl)phenylacetamidine with sodium hydroxide according to the procedure of Example 1 affords a 41% yield of N-(3,4-dichlorostyryl)phenylacetamidine hydrochloride, m.p. 216°–219° C., from isopropanol. The hydrochloride is taken up in acetone, made basic with ammonium hydroxide and the free base extracted with ethyl acetate. After washing with water, the ethyl acetate extract is dried and made acid with isethionic acid to provide the isethionate salt. Analytically pure N-(3,4-DICHLOROSTYRYL)PHENYLACETAMIDINE ISETHIONATE is obtained by crystallization from acetonitrile, m.p. 132.5°–134.5° C.

Analysis. Calcd. for $C_{16}H_{14}Cl_2N_2 \cdot C_2H_6O_4S$ (percent): C, 50.12; H, 4.67; N, 6.50. Found (percent): C, 50.30; H, 4.78; N, 6.64.

NMR (DMSO-$d_6$, TMS): 2.69t (6.6 Hz), 3.67t (6.6 Hz), 3.82m, 6.52d (13.9 Hz), 7.47m, 9.42bs, 9.78bs, 11.55bs.

EXAMPLE 6

N-(3,4-dichlorostyrylsulfonyl)benzamidine treated with sodium hydroxide according to the procedure of Example 1 provides N-(3,4-DICHLOROSTYRYL)-BENZAMIDINE HYDROCHLORIDE, m.p. 243.0°–248.5° C. (dec.)(corr.), from ethanol-methanol-isopropyl ether.

Analysis. Calcd. for $C_{15}H_{12}Cl_2N_2 \cdot HCl$ (percent): C, 54.99; H, 4.00; N, 8.56. Found (percent): C, 55.09; H, 4.00; N, 8.55.

NMR (DMSO-$d_6$, TMS): 6.89d (14.0 Hz), 7.83m, 8.38bd (14.0 Hz), 10.35bs, 12.10bs.

EXAMPLE 7

N-(3,4-dichlorostyrylsulfonyl)-3,4-dimethoxybenzamidine treated with sodium hydroxide according to the procedure of Example 1 provides a 64% yield of N-(3,4-DICHLOROSTYRYL)-3,4-DIMETHOX- YBENZAMIDINE HYDROCHLORIDE, m.p. 239.0°–240.0° C., (corr.), from methanol-isopropyl ether.

Analysis. Calcd. for $C_{17}H_{16}Cl_2N_2O_2 \cdot HCl$ (percent): C, 52.66; H, 4.42; N, 7.23. Found (percent): C, 52.56; H, 4.45; N, 7.22.

NMR (DMSO-$d_6$, TMS): 3.92s, 6.93d (14.0 Hz), 7.65m, 8.21bd (14.0 Hz), 10.20bs, 11.93bs.

EXAMPLE 8

N-(4-nitrostyrylsulfonyl)acetamidine treated with sodium hydroxide according to the procedure of Example 1 provides N-(4-nitrostyryl)acetamidine free base, m.p. 142°–143° C. Conversion of the free base to the hydrochloride salt affords N-(4-NITROSTYRYL)ACETAMIDINE HYDROCHLORIDE, m.p. 247.0°–247.5° C. (dec.)(corr.), from methanol.

Analysis. Calcd. for $C_{10}H_{11}N_3O_2 \cdot HCl$ (percent): C, 49.69; H, 5.01; N, 17.39. Found (percent): C, 49.69; H, 4.95; N, 17.33.

NMR (DMSO-$d_6$, TMS): 2.39s, 6.73d (14.1 Hz), 8.04d (14.1 Hz), 8.07m, 9.92bs, 11.95bs.

EXAMPLE 9

A suspension of 4-amino-N-(4-nitrostyrylsulfonyl)benzamidine (6.9 g., 0.02 mole) in 120 ml. of acetone is stirred with 50% sodium hydroxide (6.4 g., 0.08 mole) in 40 ml. of water for 1 hr. Concentration of the reaction mixture affords a residue which is stirred with 50 ml. of water, filtered, washed with water, and dried. Trituration of the dried filter cake with isopropyl alcohol yields 5.3 g. (95%) of N-(4-nitrostyryl)-4-aminobenzamidine free base, m.p. 195°–197° C. (dec.) The free base (5.0 g.) dissolved in 400 ml. of hot 1:1 methanolacetone and acidified with ethanolic hydrogen chloride provides 3.5 g. of analytically pure 4-AMINO-N-(4-NITROSTYRYL)BENZAMIDINE HYDROCHLORIDE as a yellow solid, m.p. 247°–248° C. (dec.)(corr.) Concentration of the mother liquors and trituration of the residue provided an additional 2.6 g. of the hydrochloride salt.

Analysis. Calcd. for $C_{15}H_{14}N_4O_2 \cdot HCl$ (percent): C, 56.50; H, 4.74; N, 17.58. Found (percent): C, 56.89; H, 4.70; N, 17.74.

NMR (DMSO-$d_6$, TMS): 3.83bs, 6.76m, 7.88m, 9.68bs, 11.37bs.

EXAMPLE 10

N-(2-nitrostyrylsulfonyl)acetamidine treated with sodium hydroxide according to the procedure of Example 9 provides N-(2-NITROSTYRYL)ACETAMIDINE HYDROCHLORIDE, m.p. 227°–229° C. (dec.)(corr.), from ethanol-isopropyl ether.

Analysis. Calcd. for $C_{10}H_{11}N_3O_2 \cdot HCl$ (percent): C, 49.69; H, 5.01; N, 17.39. Found (percent): C, 49.39; H, 5.14; N, 17.10.

NMR (DMSO-$d_6$, TMS): 2.36s, 7.02d (13.9 Hz), 7.93m, 10.18bs, 11.97bs.

EXAMPLE 11

N-(2-nitrostyrylsulfonyl)benzamidine treated with sodium hydroxide according to the procedure of Example 9 provides a 78% analytical yield of N-(2-NITROSTYRYL)BENZAMIDINE HYDROCHLORIDE, m.p. 219.5°–221.5° C. (dec.)(corr.), from methanol-isopropyl ether.

Analysis. Calcd. for $C_{15}H_{13}N_3O_2 \cdot HCl$ (percent): C, 59.32; H, 4.65; N, 13.84. Found (percent): C, 59.04; H, 4.83; N, 13.72.

NMR (DMSO-$d_6$, TMS): 7.25d (13.9 Hz), 7.87m, 10.50bs, 11.83bs.

EXAMPLE 12

N-(4-nitrostyrylsulfonyl)benzamidine treated with sodium hydroxide according to the procedure of Example 9 provides N-(4-nitrostyryl)benzamidine free base, m.p. 163°–165° C. N-(4-Nitrostyryl)benzamidine hydrochloride obtained from the free base in the usual manner has a melting point of 255°–257° C. The free base treated with a slight excess of isethionic acid in methanol affords N-(4-NITROSTYRYL)BENZAMIDINE ISETHIONATE, m.p. 204°–206.5° C. (dec.)(corr.), from methanol-isopropyl ether.

Analysis. Calcd. for $C_{15}H_{13}N_3O_2 \cdot C_2H_6O_4S$ (percent): C, 51.90; H, 4.86; N, 10.69. Found (percent): C, 51.56; H, 4.94; N, 10.54.

NMR (DMSO-$d_6$, TMS): 2.68t (6.7 Hz), 3.52t (6.7 Hz), 4.43s, 6.89d (14.0 Hz), 8.05m, 10.17bs, 11.83bs.

EXAMPLE 13

A solution of 4nitro-N-(4nitrostyrylsulfonyl)benzamidine (15.0 g., 0.04 mole) and 100 ml. of 2N sodium hydroxide in 200 ml. of acetone is stirred at 25° C. for a period of 1 hr. Acetone is removed under reduced pressure, the mixture filtered and the filter cake washed with water and dried affording 8.4 g. (68% yield) of 4-nitro-N-(4-nitrostyryl)benzamidine free base, m.p. 214°–216° C. 4-Nitro-N-(4-nitrostyryl)benzamidine hydrochloride obtained in the usual manner has a melting point of 243°–244° C. (dec.). The free base taken up in methanol and acidified with isethionic acid provides 4-NITRO-N-(4-NITROSTYRYL)BENZAMIDINE ISETHIONATE, m.p. 206.5°–208° C., (corr.).

Analysis. Calcd. for $C_{15}H_{12}N_4O_4 \cdot C_2H_6O_4S$ (percent): C, 46.57; H, 4.14; N, 12.77. Found (percent): C, 46.17; H, 4.27; N, 12.71.

NMR (DMSO-$d_6$, TMS): 2.63t (6.7 Hz), 3.62t (6.7 Hz), 3.88s, 6.78d (14.0 Hz), 7.93m, 8.37bd (14.0 Hz), 10.33bs.

EXAMPLE 14

3,5-Diamino-N-(4-nitrostyrylsulfonyl)benzamidine treated with sodium hydroxide according to the procedure of Example 9 affords 3,5-diamino-N-(4-nitrostyryl)benzamidine free base, m.p. 121°–126° C. (dec.) in a yield of 75%. Conversion of the free base with ethanolic hydrogen chloride in acetone affords 3,5-DIAMINO-N-(4-NITROSTYRYL)BENZAMIDINE TRIHYDROCHLORIDE, m.p. 210.5°–214.5° C. (dec.)(corr.), from 90% ethanol.

Analysis. Calcd. for $C_{15}H_{15}N_5O_2 \cdot 3HCl$ (percent): C, 44.29; H, 4.46; N, 17.22. Found (percent): C, 44.35; H, 4.86; N, 17.06.

NMR (DMSO-$d_6$, TMS): 5.82bs, 6.73m, 7.97m, 10.08bs, 10.45bs.

EXAMPLE 15

3-Nitro-N-(4-nitrostyrylsulfonyl)benzamidine treated with sodium hydroxide according to the procedure of Example 9 provides 3nitro-N-(4-nitrostyryl)benzamidine free base, m.p. 152°–155° C. The free base in acetone acidified with isethionic acid provides 3-NITRO-N-(4-NITROSTYRYL)BENZAMIDINE ISETHI- ONATE MONOHYDRATE, m.p. 195.0°–198.0° C. (corr.), from ethanol.

Analysis. Calcd. for $C_{15}H_{12}N_4O_4 \cdot HOC_2H_4SO_3H \cdot H_2O$ (percent): C, 44.73; H, 4.42; N, 12.27. Found (percent): C, 44.90; H, 4.20; N, 12.05.

NMR (DMSO-$d_6$, TMS): 2.62t (6.7 Hz), 3.62t (6.7 Hz), 3.79s, 6.80d (14.0 Hz), 8.07m, 10.25bs.

EXAMPLE 16

3-Amino-N-(4-nitrostyrylsulfonyl)benzamidine treated with sodium hydroxide according to the procedure of Example 9 provides 3-amino-N-(4-nitrostyryl)benzamidine free base, m.p. 146°–148° C. in 79% yield, from isopropyl alcohol-ether. Conversion of the free base to the hydrochloride salt with ethanolic hydrogen chloride affords 3-AMINO-N-(4-NITROSTYRYL)BENZAMIDINE DIHYDROCHLORIDE MONOHYDRATE, m.p. 183.0°–192.5° C. (dec.)(corr.).

Analysis. Calcd. for $C_{15}H_{14}N_4O_2 \cdot 2HCl \cdot H_2O$ (percent): C, 48.27; H, 4.86; N, 15.02. Found (percent): C, 47.99; H, 4.55; N, 14.96.

NMR (DMSO-$d_6$, TMS): 6.80d (14.0 Hz), 7.77m, 3.90bs, 10.25bs.

EXAMPLE 17

4-(Dimethylamino)-N-(4-nitrostyrylsulfonyl)benzamidine treated with sodium hydroxide according to the procedure of Example 9 provides 4-(dimethylamino)-N-(4-nitrostyryl)benzamidine free base, m.p. 191°–193° C. Acidification of the free base in methanol with isethionic acid affords 4-(DIMETHYLAMINO)-N-(4-NITROSTYRYL)BENZAMIDINE ISETHIONATE, m.p. 260.5°–262.5° C. (dec.)(corr.), from methanol-isopropyl ether.

Analysis. Calcd. for $C_{17}H_{18}N_4O_2 \cdot HOC_2H_4SO_3H$ (percent): C, 52.28, H, 5.54; N, 12.83. Found (percent): C, 52.44; H, 5.54; N, 12.82.

NMR (DMSO-$d_6$, TMS): 2.63t (6.7 Hz), 3.64t (6.7 Hz), 4.38s, 3.04s, 6.73m, 7.92m, 11.17bs.

EXAMPLE 18

N-(4-Nitrostyrylsulfonyl)cinnamamidine treated with sodium hydroxide according to the procedure of Example 9 provides N-(4-nitrostyryl)cinnamamidine free base, m.p. 120°–125° C. (dec.). Acidification of the free base in acetone with isethionic acid affords N-(4-NITROSTYRYL)CINNAMAMIDINE ISETHIONATE, m.p. 224.5°–228.0° C. (corr.), from methanol.

Analysis. Calcd. for $C_{17}H_{15}N_3O_2 \cdot HOC_2H_4SO_3H$ (percent): C, 54.41; H, 5.05; N, 10.02. Found (percent): C, 54.29; H, 5.09; N, 9.84.

NMR (DMSO-$d_6$, TMS): 2.73t (6.7 Hz), 3.69t (6.7 Hz), 4.18bs, 6.69d (13.9 Hz), 6.85d (16.2 Hz), 7.83m, 9.68bs.

EXAMPLE 19

A nitrogen atmosphere is employed throughout the reaction. A solution of sodium borohydride (3.8 g., 0.1 mole) in 10 ml. of water is added to a suspension of about 200 mg. of 10% palladium on carbon in 10 ml. of water. After 5 min., 200 ml. of methanol is added followed by portion-wise addition of finely powdered N-(4-nitrostyryl)benzamidine (8.0 g., 0.03 mole) over a period of 5 min. During the addition, the mixture refluxes and continues to boil for about 5–10 min. thereafter. The reaction mixture is stirred without external heating for 0.5 hr., filtered through celite, concentrated under reduced pressure and the residue stirred with 25 ml. of water and filtered. The filter cake washed with cold water, dried, and triturated with isopropyl alcohol provides 6.8 g. (86% yield) of N-(4-aminostyryl)benzamidine free base, m.p. 166°–168° C. Treating the free base in methanol with ethanolic hydrogen chloride and evaporating the solvent under reduced pressure provides the crude hydrochloride. Analytically pure N-(4-AMINOSTYRYL)BENZAMIDINE DIHYDROCHLORIDE, m.p. 217.5°–219.5° C. (dec.)(corr.), (60% yield) is obtained by first triturating the crude hydrochloride with acetone and then recrystallizing from methanol-isopropyl ether.

Analysis. Calcd. for $C_{15}H_{15}N_3 \cdot 2HCl$ (percent): C, 58.06; H, 5.53; N, 13.55. Found (percent): C, 58.43; H, 5.60; n, 13.36.

NMR (DMSO-$d_6$, TMS): 6.97d (14.0 Hz), 7.70m, 9.53bs, 10.18bs, 10.57bs, 12.00bs.

EXAMPLE 20

Reduction of N-(2-nitrostyrylsulfonyl)benzamidine with sodium borohydride according to the procedure of Example 19 provides N-(2-AMINOSTYRYL)BENZAMIDINE DIHYDROCHLORIDE, m.p. 226.5°–227.5° C. (dec.)(corr.), from methanol-isopropyl ether.

Analysis. Calcd. for $C_{15}H_{15}N_3 \cdot 2HCl$ (percent): C, 58.06; H, 5.53; N, 13.55. Found (percent): C, 58.30; H, 5.44; N, 13.71.

NMR (DMSO-$d_6$, TMS): 6.84d (14.0 Hz), 7.58m, 9.92bm, 11.75bs.

EXAMPLE 21

Reduction of 4-nitro-N-(4-nitrostyryl)benzamidine with sodium borohydride according to the procedure of Example 19 affords 4-AMINO-N-(4-AMINOSTYRYL)BENZAMIDINE TRIHYDROCHLORIDE, m.p. 259.0° C. (dec.)(corr.), from methanol-isopropyl ether.

Analysis. Calcd. for $C_{15}H_{16}N_4 \cdot 3HCl$ (percent): C, 49.80; H, 5.30; N, 15.49. Found (percent): C, 49.60; H, 5.34; N, 15.66.

NMR (DMSO-$d_6$, TMS): 6.80m, 7.62m, 9.53bs, 9.75bs, 11.33bs.

EXAMPLE 22

Reduction of 3,5-diamino-N-(4-nitrostyryl)benzamidine with sodium borohydride according to the procedure of Example 19 provides 3,5-DIAMINO-N-(4-AMINOSTYRYL)BENZAMIDINE TRIHYDROCHLORIDE, m.p. 286.5°–288.0° C. (dec.)(corr.), from aqueous ethanol.

Analysis. Calcd. for $C_{15}H_{17}N_5 \cdot 3HCl$ (percent): C, 47.82; H, 5.35; N, 18.60. Found (percent): C, 47.60; H, 5.44; N, 18.54.

NMR ($D_2O$, DSS): 4.67s, 6.70d (14.0 Hz), 7.47m,

EXAMPLE 23

Reduction of 3-nitro-N-(4-aminostyryl)benzamidine with sodium borohydride according to the procedure of Example 19 provides 3-AMINO-N-(4-AMINOSTYRYL)BENZAMIDINE TRIHYDROCHLORIDE MONOHYDRATE, m.p. 224.5°–226.5° C. (dec.)(corr.), from methanol-isopropyl acetate.

Analysis. Calcd. for $C_{15}H_{16}N_4 \cdot 3H_2O$ (percent): C, 47.44; H, 5.58; N, 14.76; $H_2O$, 4.74. Found (percent): C, 47.40; H, 5.65; N, 14.56; $H_2O$, 4.68.

NMR ($D_2O$, DSS): 4.67s, 6.68d (14.0 Hz), 7.43m.

EXAMPLE 24

Reduction of N-(nitrostyryl)-2-naphthamidine according to the procedure of Example 19 with sodium borohydride provides N-(4-aminostyryl)-2-naphthamidine free base, m.p. 151°–153° C. Acidification of the free base in acetone with 5N hydrochloric acid affords N-(4-AMINOSTYRYL)-2-NAPHTHAMIDINE DIHYDROCHLORIDE, m.p. 235°–237° C. (dec.)(corr.), from methanol-isopropyl ether.

Analysis. Calcd. for $C_{19}H_{17}N_3 \cdot 2HCl$ (percent): C, 63.33; H, 5.32; N, 11.66. Found (percent): C, 63.41; H, 5.25; N, 11.65.

NMR (DMSO-$d_6$, TMS): 6.86d (14.0 Hz), 7.71m, 8.50d (2.0 Hz), 9.13bs, 10.08bs, 10.42bs. 11.85bs.

EXAMPLE 25

A solution of N-(4-aminostyryl)benzamidine (2.4 g., 0.01 mole) in 25 ml. of acetic acid and 5 ml. of acetic anhydride is heated at 100° C. for a period of 15 min., cooled and quenched in 50 ml. of iced-water. The yellow solution thus obtained is acidified with 3N hydrochloric acid providing a yellow precipitate which is collected, triturated with acetone and crystallized from methanol-ethanol to yield 2.0 g., (63%) of analytically pure N-(4-ACETAMIDOSTYRYL)BENZAMIDINE HYDROCHLORIDE, m.p. 249°–251° C. (dec.)(corr.).

Analysis. Calcd. for $C_{17}H_{17}N_3O \cdot HCl$ (percent): C, 64.66; H, 5.74; N, 13.30. Found (percent): C, 64.72; H, 6.05; N, 13.11.

NMR (DMSO-$d_6$, TMS): 2.05s, 6.74d (13.5 Hz), 7.64m, 9.83bm, 10.05s, 11.55bm.

EXAMPLE 26

The following styrylamidine products of Formula I are obtained by treating the enumerated styrylsulfonylamidine precursor with sodium hydroxide in dimethylsulfoxide according to the procedure of Example 1:

(a) N-(4-CARBAMOYLSTYRYL)ACETAMIDINE from N-(4-carbamoylstyrylsulfonyl)acetamidine;
(b) N-(4-SULFAMOYLSTYRYL)ACETAMIDINE from N-(4-sulfamoylstyrylsulfonyl)acetamidine;
(c) N-(3-METHYLSULFONYLSTYRYL)ACETAMIDINE from N-(3-methylsulfonylstyrylsulfonyl)acetamidine;
(d) N-(4-CYCLOHEXYLSTYRYL)ACETAMIDINE from N-(4-cyclohexylstyrylsulfonyl)acetamidine;
(e) N-(3-Bromo-4-cyclohexylstyrylsulfonyl)acetamidine provides N-(3-BROMO-4-CYCLOHEXYLSTYRYL)ACETAMIDINE HYDROCHLORIDE, m.p. 212°–215° C. (dec.)(corr.).

Analysis. Found (percent): C, 53.46; H, 6.22; N, 7.72.
NMR (DMSO-$d_6$, TMS): 1.60m, 2.29s, 2.82m, 6.46d (14.0 Hz), 7.5bm, 10.25bs.

(f) N-(STYRYL)-4-CHLOROBENZAMIDINE from N-(styrylsulfonyl)-4-chlorobenzamidine;
(g) N-(STYRYL)-3-ACETAMIDOBENZAMIDINE from N-(styrylsulfonyl)-3-acetamidobenzamidine;
(h) N-(STYRYL)-3,4-DICHLOROBENZAMIDINE from N-(styrylsulfonyl)-3,4-dichlorobenzamidine;
(i) N-(4-(NITROSTYRYL)-4-STYRYLBENZAMIDINE from N-(4-nitrostyrylsulfonyl)-4-styrylbenzamidine;
(j) N-(4-NITROSTYRYL)-4-(PHENYLBUTADIENYL)BENZAMIDINE from N-(4-nitrostyrylsulfonyl)-4-(phenylbutadienyl)benzamidine;
(k) N-(2-FLUOROSTYRYL)BENZAMIDINE from N-(2-fluorostyrylsulfonyl)benzamidine;
(l) N-(2,5-DICHLOROSTYRYL)BENZAMIDINE from N-(2,4-dichlorostyrylsulfonyl)benzamidine;
(m) N-(STYRYL)-4-(di-n-BUTYLAMINO)BENZAMIDINE from N-(styrylsulfonyl)-4-(di-n-butylamino)benzamidine;
(n) N-[3-(2-METHYLPROPIONAMIDO)STYRYL]ACETAMIDINE from N-[3-(2-methylpropionamido)styrylsulfonyl]acetamidine;
(o) N-(STYRYL)-2-sec.-BUTYRAMIDINE from N-(styrylsulfonyl)sec.-butyramidine;
(p) N-[(2,6-DICHLOROSTYRYL)SULFONYL]ACETAMIDINE provides N-(2,6-dichlorostyryl)acetamidine hydrochloride, m.p. 154.5°–158.5° C. (corr.).

Analysis. Found (percent): C, 45.20; H, 4.13; N, 10.66.
NMR (DMSO-$d_6$, TMS): 2.35s, 6.65d (13.8 Hz), 7.40m, 9.5bs, 9.8bs, 12.0.

EXAMPLE 27

Reaction of the aminostyrylamidines enumerated below with acetic anhydride according to the procedure of Example 25 provides the following acetamidostyrylamidine products of Formula I:

(a) N-(4-ACETAMIDOSTYRYL)-4-STYRYLBENZAMIDINE from N-(4-aminostyryl)-4-styrylbenzamidine;
(b) N-(4-ACETAMIDOSTYRYL)-4-(PHENYLBUTADIENYL)BENZAMIDINE from N-(4-aminostyryl)-4-(phenylbutadienyl)benzamidine.

EXAMPLE 28

Reduction of the nitrostyrylamidines enumerated below with sodium borohydride according to the procedure of Example 19 provides the following aminostyrylamidines of Formula I:

(a) N-(4-(AMINOSTYRYL)-4-STYRYLBENZAMIDINE from N-(nitrostyryl)-4-styrylbenzamidine;
(b) N-(4-AMINOSTYRYL)-4-(PHENYLBUTADIENYL)BENZAMIDINE from N-(4-nitrostyryl)-4-(phenylbutadienyl)benzamidine.

EXAMPLE 29

Preparation of Styrylsulfonylamidines (a) 4-Nitrobenzamidine hydrochloride obtained according to method of L. Weintraub, et al., J. Org. Chem., 33, 1679 (1968) is hydrogenated in methanol solution in a Parr Apparatus employing a 10% palladium on carbon catalyst to provide 4-aminobenzamidine hydrochloride.

Addition of 50% sodium hydroxide (4.0 g., 0.05 mole) to a solution of 4-aminobenzamidine hydrochloride (0.5 mole) in 10 ml. of water affords 4-aminobenzamidine free base. Acetone (50 ml.) is added to the liberated free base and the mixture cooled to 5° C. 4-Nitrostyrylsulfonyl chloride is added to the mixture in a period of 5 min. while maintaining a temperature below 15° C. The mixture is stirred for 10 min., the reaction mixture concentrated under reduced pressure provides a residue which diluted with 100 ml. of water and neutralized with 3N hyrochloric acid affords a pale yellow solid precipitate. The precipitate is collected, washed thoroughly with water and then triturated first with isopropanol and then with ether to yield 7.3 g. (84%) of N-(4-NITROSTYRYLSULFONYL)-4-AMINOBENZAMIDINE, m.p. 188°–189° C. (b) A mixture of acetamidine hydrochloride (28.8 g., 0.15 mole) and 50% sodium hydroxide (12.0 g., 0.15 mole) in 150 ml. of acetone is stirred for a period of 10 min. to liberate the free base. A solution of styrylsulfonyl chloride (10.1 g., 0.05 mole) in 50 ml. of acetone is added dropwise to the mixture at a temperature of 20°–25° C. with stirring. After further stirring for 10 min., the mixture is concentrated under reduced pressure to remove acetone, the concentrate diluted with 200 ml. of water and acidified with 3N hydrochloric acid to provide a precipitate. The precipitate is collected, dissolved in chloroform and the chloroform extract dried. Evaporation of the chloroform solvent under reduced pressure provides a white solid, m.p. 130°–134° C. which is crystallized from isopropyl acetate affording 8.5 g. (76% yield) of N-(STYRYLSULFONYL)ACETAMIDINE, m.p. 134.5°–137.0° C. (corr.).

Analysis. Calcd. for $C_{10}H_{12}N_2O_2S$ (percent): C, 53.55; H, 5.39; N, 12.49. Found (percent): C, 53.37; H, 5.30; N, 12.54.

NMR ($CDCl_3$, TMS): 2.16s, 6.73bs, 6.92d (15.5 Hz), 7.45m, 7.64d (15.5 Hz), 7.84bs.

(c) Reaction of benzamidine and styrylsulfonyl chloride according to the above procedure provides N-(STYRYLSULFONYL)BENZAMIDINE, m.p. 192.5°–194.5° C. (corr.), crystallized from acetone.

Analysis. Calcd. for $C_{15}H_{14}N_2O_2S$ (percent): C, 62.91; H, 4.93; N, 9.79. Found (percent): C, 63.13; H, 5.06; N, 9.64.

NMR (DMSO-$d_6$, TMS): 7.4–8.1m, 8.20bs. 9.20bs.

(d) Reaction of acetamidine with 4-nitrostyrylsulfonyl chloride according to the above procedure provides N-(4-NITROSTYRYLSULFONYL)ACETAMIDINE, m.p. 203.0°–203.5° C. (dec.)(corr.), crystallized from acetonitrile.

Analysis. Calcd. for $C_{10}H_{11}N_3O_4S$ (percent): C, 44.59; H, 4.12; N, 15.61. Found (percent): C, 44.85; H, 4.21; N, 15.74.

NMR (DMSO-$d_6$, TMS): 2.16s, 7.56s, 8.15m, 8.62bs.

(e) Reaction of acetamidine with 3,4-dichlorostyrylsulfonyl chloride according to the above procedure affords N-[(3,4-DICHLOROSTYRYL)SULFONYL]-ACETAMIDINE, m.p. 197.5°–198.5° C. (corr.), crystallized from acetone-isopropanol.

Analysis. Calcd. for $C_{10}H_{10}Cl_2N_2O_2S$ (percent): C, 40.96; H, 3.44; N, 9.56. Found (percent): C, 41.15; H, 3.64; N, 9.49. NMR (DMSO-$d_6$, TMS): 2.14s, 7.43s, 7.73m, 7.96bs, 8.08m, 8.57bs.

(f) Reaction of acetamidine with 4-chlorostyrylsulfonyl chloride according to the above procedure affords N-[(4-CHLOROSTYRYL)SULFONYL]ACETAMIDINE, m.p. 161°–163° C., crystallized from ethyl acetate.

(g) Reaction of phenylacetamidine benzenesulfonate, obtained according to the method of P. Oxley and W. F. Short, J. Chem. Soc., 147 (1946), with 3,4-dichlorostyrylsulfonyl cloride according to the above procedure affords N-[(3,4-DICHLOROSTYRYL)SULFONYL]-PHENYLACETAMIDINE, m.p. 151°–155° C.

(h) Reaction of benzamidine with 3,4-dichlorostyrylsulfonyl chloride according to the above procedure affords N-[(3,4-DICHLOROSTYRYL)SULFONYL]-BENZAMIDINE, m.p. 144°–146° C.

(i) Reaction of acetamidine with 2-nitrostyrylsulfonyl chloride according to the above procedure affords N-(2-NITROSTYRYLSULFONYL)ACETAMIDINE, m.p. 175°–178° C.

(j) Reaction of benzamidine with 4-nitrostyrylsulfonyl chloride according to the above procedure affords N-(4-NITROSTYRYLSULFONYL)BENZAMIDINE, m.p. 173°–175° C., by triturating with methanol.

(k) 4-Nitrostyrylsulfonyl chloride (2.5 g., 0.01 mole) is added portion-wise to a solution of 4-nitrobenzamidine (1.65 g., 0.01 mole), prepared according to the procedure of L. Weintraub, et al., J. Org. Chem., 33, 1679 (1968), and triethylamine (1.01 g., 0.01 mole) in 50 ml. of acetone at 10° C. After stirring for a period of 1 hr. at 25° C., the mixture is concentrated under reduced pressure and the residual material stirred with water and collected. Triturating the filter cake with acetone provides N-(4-NITROSTYRYLSULFONYL)-4-NITROBENZAMIDINE, m.p. 173°–177° C.

(l) Reaction of 3-nitrobenzamidine with 4-nitrostyrylsulfonyl chloride according to the above procedure provides N-(4-NITROSTYRYLSULFONYL)-3-NITROBENZAMIDINE, m.p. 230°–232° C.

(m) Reaction of 3-aminobenzamidine, obtained by catalytic reduction of 3-nitrobenzamidine in methanol in a Parr Apparatus employing 10% palladium on carbon catalyst, with 4-nitrostyrylsulfonyl chloride according to the above procedure affords N-(4-NITROSTYRYLSULFONYL)-3-AMINOBENZAMIDINE, m.p. 162°–170° C., by triturating with isopropanol.

(n) Reaction of 4-(N,N-dimethylamino)benzamidine, obtained according to the procedure of "Organic Synthesis", Coll. Vol. 1, 2nd Ed., page 5, (Wiley, 1932), with 4-nitrostyrylsulfonyl chloride according to the above procedure affords N-(4-NITROSTYRYLSULFONYL)-4-DIMETHYLAMINOBENZAMIDINE, m.p. 192°–196° C., by triturating with acetone.

(o) Reacton of cinnamamidine, obtained according to the procedure of "Organic Synthesis", Coll. Vol. 1, 2nd, Ed. page 5, (Wiley, 1932), with 4-nitrostyrylsulfonyl chloride by the above procedure affords N-(4-NITROSTYRYLSULFONYL)CINNAMAMIDINE, m.p. 188°–192° C., by triturating with ethyl acetate.

(p) Reaction of β-naphthamidine with 4-nitrostyrylsulfonyl chloride according to the above procedure affords N-(4-NITROSTYRYLSULFONYL)-β-NAPHTHAMIDINE, m.p. 180°–182.5° C., by triturating with isopropanol.

(q) Reaction of 3,5-diaminobenzamidine obtained by catalytic reduction of 3,5-dinitrobenzamidine benzenesulfonate, with 4-nitrostyrylsulfonyl chloride according to the above procedure affords N-(4-NITROSTYRYLSULFONYL)-3,5-DIAMINOBENZAMIDINE.

(r) Hydrogen chloride is bubbled through a mixture of 4-cyanostilbene (13.5 g., 0.065 mole), obtained according to the method of Belgian Pat. No. 641,415 (Chem. Abs. 63: 3092g (1965)), in 35 ml. of dry benzene and 17.5 ml. of absolute ethanol at 0° to 5° C. for a period of 3 hr. The reaction is maintained at 0° to 5° C. for 48 hr. and the solvent and excess hydrogen chloride removed under reduced pressure. The residue stirred with 50 ml. of dry benzene and collected provides 13.0 g. of ethyl-4-styrylbenzimidate hydrochloride. A methanol solution of the benzimidate salt is cooled to 5° to 10° C., saturated with ammonia and heated at a temperature of 100° C. for a period of 3 hr. in an enclosed container. Concentration of the reaction mixture provides 4-styrylbenzamidine hydrochloride.

Reaction of 4-styrylbenzamidine with 4-nitrostyrylsulfonyl chloride according to the procedure of Example 29 (a) provides N-(4-NITROSTYRYLSULFONYL)-4-STYRYLBENZAMIDINE.

(s) By substituting 4-(4-phenylbuta-1,3-dienyl)benzonitrile for 4-cyanostilbene according to Example 29 (r) there is obtained ethyl-4-(4-phenylbuta-1,3-dienyl)-benzimidate hydrochloride, m.p. 245°–260° C. (dec.) by triturating with acetone. The ethylbenzimidate salt is converted to 4-(4-phenylbuta-1,3-dienyl)benzamidine hydrochloride by dissolving in methanol saturated with ammonia.

Reaction of 4-(4-phenylbuta-1,3-dienyl) benzamidine with 4-nitrostyrylsulfonyl chloride according to the procedure of Example 29 (a) provides N-(4-NITROSTYRYLSULFONYL)-4-PHENYLBUTADIENYLBENZAMIDINE.

(t) Ammonia is bubbled through a solution of 3,4-dichlorostyrylsulfonyl chloride (27.2 g., 0.1 mole) in 250 ml. of ether for a period of 30 min. at about 20° C. The solvent is evaporated and the residue stirred with water, collected and dried at 100° C. under vacuum affords 24.6 g. (97% yield) of 3,4-dichlorostyrylsulfonamide, m.p. 127°–130° C.

A mixture of 3,4-dichlorostyrylsulfonamide (12.6 g., 0.05 mole) and 3,4-dimethoxybenzoyl chloride (11.0 g., 0.055 mole) in 15 ml. of phosphorous oxychloride is heated at steam bath temperature for a period of 30 min. Excess phosphorous oxychloride is removed under reduced pressure and dry benzene added. The benzene is evaporated and the treatment repeated two times. Benzene (50 ml.) is added to the residue thus obtained and the insoluble solid collected providing 14.6 g. (70% yield) of N-(3,4-dichlorostyrylsulfonyl)-3,4-dimethoxybenzamide, m.p. 145°–147° C.

A suspension of N-(3,4-dichlorostyrylsulfonyl)-3,4-dimethoxybenzamide (8.3 g., 0.02 mole) in 100 ml. of dry benzene is stirred and refluxed with phosphorus pentachloride (4.6 g., 0.022 mole) for a period of 1.5 hr. providing a clear solution which is concentrated under reduced pressure. Benzene is added to the residue and evaporated. The benzene treatment is repeated several times and the residue thus obtained triturated with isopropyl ether provides a quantitative yield of N-(3,4-dichlorostyrylsulfonyl)-3,4-dimethoxybenzimidoyl chloride, m.p. 120°–125° C.

Ammonium gas is bubbled through a solution of N-(3,4-dichlorostyrylsulfonyl)-3,4-dimethoxybenzimidoyl chloride (8.7 g., 0.02 mole) in 100 ml. of dry benzene for a period of 1 hr. The solvent evaporated under reduced pressure and the solid residue stirred with 50 ml. of water and filtered affords 8.0 g. (96% yield) of N-(3,4-DICHLOROSTYRYLSULFONYL)-3,4-DIMETHOXYBENZAMIDINE, m.p. 205°–210° C. A sample crystallized from acetonitrile has a melting point of m.p. 208°–211° C.

(u) Reaction of acetamidine with 2,6-dichlorostyrylsulfonyl chloride according to the procedure of Example 29(b) affords N'-[(2,6-dichlorostyryl)sulfonyl]-acetamidine, m.p. 154.5°–158.5° C. (corr.), from absolute ethanol.

Analysis. Calcd. for $C_{10}H_{10}Cl_2N_2O_2S$ (percent): C, 40.96, H, 3.44; N, 9.56. Found (percent): C, 40.60; H, 3.36; N, 9.37.

EXAMPLE 30

Reaction of the styrylsulfonyl chlorides and amidines enumerated below according to the procedures set forth in Example 29 provides the following styrylsulfonylamidine precursors of the products of Formula I:

(a) N-(4-CARBAMOYLSTYRYLSULFONYL)ACETAMIDINE from 4-carbamoylstyrylsulfonyl chloride and acetamidine;

(b) N-(4-SULFAMOYLSTYRYLSULFONYL)ACETAMIDINE from 4-sulfamoylstyrylsulfonyl chloride and acetamidine;

(c) N-(3-METHYLSULFONYLSTYRYLSULFONYL)ACETAMIDINE from 3-methylsulfonylstyrylsulfonyl chloride and acetamidine;

(d) N-(4-CYCLOHEXYLSTYRYLSULFONYL)ACETAMIDINE from 4-cyclohexylstyrylsulfonyl chloride and acetamidine;

(e) N-(3-BROMO-4-CYCLOHEXYLSTYRYLSULFONYL)ACETAMIDINE, m.p. 148°–156° C., from 3-bromo-4-cyclohexylstyrylsulfonyl chloride and acetamidine;

(f) N-(STYRYLSULFONYL)-4-CHLOROBENZAMIDINE from styrylsulfonyl chloride and 4-chlorobenzamidine;

(g) N-(STYRYLSULFONYL)-3-ACETAMIDOBENZAMIDINE from sytrylsulfonyl chloride and 3-acetamidobenzamidine;

(h) N-(STYRYLSULFONYL)-3,4-DICHLOROBENZAMIDINE from styrylsulfonyl chloride and 3,4-dichlorobenzamidine;

(i) N-(4-NITROSTYRYLSULFONYL)-4-STYRYLBENZAMIDINE from 4-nitrostyrylsulfonyl chloride and 4-styrylbenzamidine;

(j) N-(4-NITROSTYRYLSULFONYL)-4-PHENYLBUTADIENYLBENZAMIDINE from 4-nitrostyrylsulfonyl chloride and 4-phenylbutadienylbenzamidine;

(k) N-(2-FLUOROSTYRYLSULFONYL)BENZAMIDINE from 2-fluorostyrylsulfonyl chloride and benzamidine;

(l) N-(2,5-DICHLOROSTYRYLSULFONYL)BENZAMIDINE from 2,5-dichlorostyrylsulfonyl chloride and benzamidine;

(m) N-(STYRYLSULFONYL)-4-(di-n-BUTYLAMINO)BENZAMIDINE from styrylsulfonyl chloride and 4-(di-n-butylamino)benzamidine;

(n) N-[3-(2-METHYLPROPIONAMIDO)STYRYLSULFONYL]ACETAMIDINE from 3-(2-methylpropionamido)styrylsulfonyl chloride and acetamidine;

(o) N-(STYRYLSULFONYL)-sec.-BUTYRAMIDINE from styrylsulfonyl chloride and sec.-butyramidine.

EXAMPLE 31

Preparation of Styrylsulfonyl Chlorides (a) 3,4-DICHLOROSTYRYLSULFONYL CHLORIDE Sulfur trioxide (20.0 g., 0.25 mol) is distilled from 20% fuming sulfuric acid into a flask containing 200 ml. of dry dichloroethane. Dioxane (21.0 g., 0.25 mole) is added dropwise to the solution of sulfur trioxide while maintaining a temperature of from −10° to 0° C. After the addition of dioxane, a solution of 3,4-dichlorostyrene (43.8 g., 0.25 mole) in 50 ml. of dichloroethane is added over a 10 min. period at 0° C. The solution is stirred for 3 hr. at 25° C., refluxed for 0.5 hr. and the poured into 400 ml. of cold water. The reaction mixture is extracted with ether, basified with 50% sodium hydroxide, and the aqueous fraction concentrated under reduced pressure to a small volume yielding 35.4 g. (51%) of the sodium salt of 3,4-dichlorostyrylsulfonic acid.

A mixture of the sodium sulfonate salt (35 g., 0.126 mole) and phosphorus pentachloride (30 g., 0.144 mole) is heated at a temperature of 100° C. for a period of 5 hr. After removal of the phosphorus oxychloride by-product under vacuum the reaction mixture is added to ice water, the resulting mass broken up and the mixture filtered. The filter cake is dissolved in ether, the ethereal solution, washed with water and dried over magnesium sulfate. Evaporation of the ether solvent provides 3,4-dichlorostyrylsulfonyl chloride, m.p. 91°–96° C. in 92% yield. A sample crystallized from chloroform melts at 95°–98° C.

(b) Substituting 4-chlorostyrene for 3,4-dichlorostyrene in the above procedure provides 4-CHLOROSTYRYLSULFONYL CHLORIDE, m.p. 133°–135° C. in 88% yield.

(c) Substituting styrene in the above procedure for 3,4-dichlorostyrene provides STYRENESULFONYL CHLORIDE, m.p. 86°–89° C. in 95% yield.

(d) Nitration of styrenesulfonyl chloride according to the procedure of F. G. Bordwell, et al., J. Amer. Chem. Soc., 68, 1778 (1946) provides 2-NITROSTYRYLSULFONYL CHLORIDE, m.p. 102–105° C., and 4-NITROSTYRYLSULFONYL CHLORIDE, m.p. 171°–174° C.

(e) Substituting 4-carbamoylstyrene for 3,4-dichlorostyrene in the above procedure provides 4-CARBAMOYLSTYRYLSULFONYL CHLORIDE.

(f) Substituting 4-sulfamoylstyrene for 3,4-dichlorostyrene in the above procedure provides 4-SULFAMOYLSTYRYLSULFONYL CHLORIDE.

(g) Substituting 3-methylsulfonylstyrene for 3,4-dichlorostyrene in the above procedure provides 3-METHYLSULFONYLSTYRYLSULFONYL CHLORIDE.

(h) Substituting 4-cyclohexylstyrene for 3,4-dichlorostyrene in the above procedure provides 4-CYCLOHEXYLSTYRYLSULFONYL CHLORIDE.

(i) Substituting 3-bromo-4-cyclohexylstyrene for 3,4-dichlorostyrene in the above procedure provides 3-BROMO-4-CYCLOHEXYLSTYRYLSULFONYL CHLORIDE, m.p. 93°–97° C.

(j) Substituting 2-fluorostyrene for 3,4-dichlorostyrene in the above procedure provides 2-FLUOROSTYRYLSULFONYL CHLORIDE.

(k) Substituting 2,5-dichlorostyrene for 3,4-dichlorostyrene in the above procedure provides 2,5-DICHLOROSTYRYLSULFONYL CHLORIDE.

(l) Substituting 3-(2-methylpropionamido)styrene for 3,4-dichlorostyrene in the above procedure provides 3-(2-METHYLPROPIONAMIDO)STYRYLSULFONYL CHLORIDE.

(m) Substituting 2,6-dichlorostyrene for 3,4-dichlorostyrene in the above procedure provides 2,6-DICHLOROSTYRYLSULFONYL CHLORIDE, m.p. 88°–90° C.

EXAMPLE 32

Preparation of N-Methyl-N-(4-nitrostyryl)benzamidine Hydrochloride (a) N-(4-Nitrostyrylsulfonyl)benzimidoyl chloride A mixture of 4-nitrostyrylsulfonamide (18.2 g., 0.08 mole), benzoyl chloride (12.6 g., 0.09 mole) and phosphorus oxychloride (13.8 g., 0.09 mole) is heated at steam bath temperature for 1.5 hr. The reaction mixture diluted with 20 ml of ethyl acetate, cooled and filtered affords 19.0 g (76% yield) of N-(4-nitrostyrylsulfonyl)benzamide, m.p. 192°–195° C., from ethyl acetate-hexane.

A suspension of N-(4-nitrostyrylsulfonyl)benzamide (14.9 g., 0.045 mole) in 500 ml. of dry benzene is refluxed and stirred with phosphorus pentachloride (10.4 g., 0.05 mole) for 8 hr. The reaction mixture after standing overnight at 25° C. provides 8.2 g. of solid, m.p. 158°–166° C. Concentration of the mother liquor to about 100 ml. provides an additional 2.5 g. of solid, m.p. 158°–161° C. The combined crude solid crystallized from ethyl acetate affords analytically pure N-(4-nitrostyrylsulfonyl)benzimidoyl chloride, m.p. 168°–175° C.

Anal. Found: C, 51.46; H, 3.09; N, 7.79.

(b) N-Methyl-N'-(4-nitrostyrylsulfonyl)benzamidine Methylamine is passed slowly into a solution of N-(4-nitrostyrylsulfonyl)benzimidoyl chloride (6.3 g., 0.018 mole) in 50 ml. of dry acetone for 5 min. at 25° C. After stirring the mixture for 25 min. at 25° C., the mixture is concentrated and 50 ml. water and 150 ml. of chloroform added. The resulting mixture is shaken vigorously and filtered. Insoluble material is triturated with 200 ml. of hot chloroform, cooled and filtered providing 0.6 g. of N-methyl-N'-(4-nitrostyrylsulfonyl)benzamidine. The chloroform fractions are combined, washed with water, dried over magnesium sulfate and concentrated under reduced pressure. Trituration of the residue thus obtained with methanol affords an additional 3.5 g. of the benzamidine. Analytically pure N-methyl-N'-(4-nitrostyrylsulfonyl)benzamidine has a melting point of 155.5°–157° C. (dec.) from acetonitrile.

Anal. Calcd. for $C_{16}H_{15}N_3O_4S$: C, 55.65; H, 4.38; N, 12.17. Found: C, 55.29; H, 4.24; N, 12.16.

NMR (DMSO-$d_6$, TMS); 2.92d (4.0 Hz), 7.12d (15.0 Hz), 7.70–7.25m, 7.85d (9.0 Hz), 8.21d (9.0 Hz), 9.00bs.

(c) N-Methyl-N-(4-nitrostyryl)benzamidine A mixture of N-methyl-N'-(4-nitrostyrylsulfonyl)benzamidine (3.45 g., 0.01 mole) in 100 ml. of acetone and 25 ml. of 10% aqueous sodium hydroxide is stirred at 25° C. for 30 min. The solvent is removed under reduced pressure and the residue diluted with water and extracted with chloroform. The chloroform extract is washed with water, dried over potassium carbonate and concentrated affording the benzamidine free base. The free base is taken up in ethanol, acidified with ethanolic hydrogen chloride and the hydrochloride salt isolated by dilution with ether. Trituration of the crude salt with acetone and crystallization from methanol-isopropyl ether provides 2.4 g. (75%) of analytically pure N-methyl-N-(4-nitrostyryl)benzamidine hydrochloride, m.p. 247.5°–249.5° C. (dec.)(corr.).

Anal. Calcd. for $C_{16}H_{15}N_3O_2 \cdot HCl$; C, 60.47; H, 5.08; N, 13.22. Found: C, 60.66; H, 5.03; N, 13.35.

NMR (DMSO-$d_6$, TMS): 3.44s, 6.90d, 7.6–8.0m, 8.22d (9.0 Hz), 10.70bs.

EXAMPLE 33

Preparation of 5,6-dihydro-4-methyl-5-(4-nitrophenyl)-3-phenyl-4H-1,2,4-thiadiazine 1,1-dioxide Methylamine is bubbled into a solution of N-(4-nitrostyrylsulfonyl)benzimidoyl chloride (5.25 g., 0.015 mole) in 100 ml. of acetone for a period of 2.5 hr. The reaction mixture is concentrated under reduced pressure, diluted with 50 ml. of water and acidified with 3N hydrochloric acid. After stirring for several minutes the acidified mixture is filtered and insolubles air dried. Trituration of this crude product with 30 ml. of isopropanol and then isopropyl ether affords 3.2 g. (61%) of 5,6-dihydro-4-methyl-5-(4-nitrophenyl)-3-phenyl-4H-1,2,4-thiadiazine 1,1-dioxide, m.p. 179°–181° C., (dec.)(corr.), from acetonitrile.

Anal. Calcd. for $C_{16}H_{15}N_3O_4S$: C, 55.64; H, 4.38; N, 12.17. Found: C, 55.77; H, 4.32; N, 12.23.

NMR (DMSO-$d_6$, TMS): 3.02s, 3.40m, 5.03dd (8.5 Hz, 6.0 Hz), 7.50s, 7.66d (8.5 Hz), 8.15d (8.5 Hz).

Oral or intraperitoneal administration of 5,6-dihydro-4-methyl-5-(4-nitrophenyl)-3-phenyl-4H-1,2,4-thiadiazine 1,1-dioxide to the mouse produced non-specific CNS depression. 5,6-Dihydro-4-methyl-5-(4-nitrophenyl)-3-phenyl-4H-1,2,4-thiadiazine 1,1-dioxide was not effective in preventing the phenylquinone writhing syndrome in mice at an oral dose of 100 mg./kg. body weight or subcutaneous dose of 6 mg./kg. body weight.

EXAMPLE 34

Treating N-isopropyl-N'-(3,4-dichlorostyrylsulfonyl)acetamidine with aqueous sodium hydroxide in acetone or dimethylsulfoxide according to the procedure of Example 32(c) provides N-isopropyl-N-(3,4-dichlorostyryl)acetamidine.

EXAMPLE 35

Treating N-methyl-N'-(3,4-dichlorostyrylsulfonyl)acetamidine with aqueous sodium hydroxide in acetone according to the procedure of Example 32(c) provides N-methyl-N-(3,4-dichlorostyryl)acetamidine.

EXAMPLE 36

N-(3,4-Dichlorostyrylsulfonyl)propionamidine treated with sodium hydroxide according to the procedure of Example 1 provides N-(3,4-DICHLOROSTYRYL)PROPIONAMIDINE HYDROCHLORIDE, m.p. 205.0°–209.0° C., (corr.), in 29% analytical yield by crystallization from isopropyl alcohol-isopropyl ether.

Analysis. Calcd. for $C_{11}H_{12}Cl_2N_2.HCl$ (percent): C, 47.25; H, 4.69; N, 10.02. Found (percent): C, 46.98; H, 4.77; N, 9.95.

NMR (DMSO-$d_6$, TMS): 1.25t (7.5 Hz), 2.60quartet (7.5 Hz), 6.56d (13.9 Hz), 7.51m, 7.92m, 9.9bs, 11.9bs.

EXAMPLE 37

N-(3,4-Dichlorostyrylsulfonyl)butyramidine treated with sodium hydroxide according to the procedure of Example 1 provides N-(3,4-DICHLOROSTYRYL)BUTYRAMIDINE HYDROCHLORIDE, m.p. 222.5°–224.5° C, in 41% analytical yield by crystallization from isopropyl alcohol-isopropyl ether.

Analysis. Calcd. for $C_{12}H_{14}Cl_2N_2.HCl$ (percent): C, 49.09; H, 5.15; N, 9.54. Found (percent): C, 48.94; H, 5.08; N, 9.74.

NMR (DMSO-$d_6$, TMS): 0.93t (7.0 Hz), 1.67m, 2.58m, 6.56d (14.0 Hz), 7.53m, 7.90m, 9.9bs, 11.9bs.

EXAMPLE 38

N-(3,4-Dichlorostyrylsulfonyl)pentanamidine treated with sodium hydroxide according to the procedure of Example 1 provides N-(3,4-DICHLOROSTYRYL)-PENTANAMIDINE HYDROCHLORIDE, m.p. 218.0°–220.0° C., (corr.), in 52% analytical yield from ethyl acetate.

Analysis. Calcd. for $C_{13}H_{16}Cl_2.HCl$ (percent): C, 50.75; H, 5.57; N, 9.10. Found (percent): C, 50.72; H, 5.74; N, 8.96.

NMR (DMSO-$d_6$, TMS): 0.90t (6.0 Hz), 1.50m, 2.59m, 6.57d (14.0 Hz), 7.53m, 7.95m, 9.9bs, 10.0bs, 12.0bd (10.0 Hz).

EXAMPLE 39

N-(3,4-Dichlorostyrylsulfonyl)-2-methylpropionamidine treated with sodium hydroxide according to the precedure of Example 1 provides N-(3,4-DICHLOROSTYRYL)-2-METHYLPROPIONAMIDINE HYDROCHLORIDE, m.p. 219.5°–222° C. (corr.), in 44% analytical yield by crystallization from acetone.

Analysis. Calcd. for $C_{12}H_{12}Cl_2N_2.HCl$ (percent): C, 49.09; H, 5.15; N, 9.54. Found (percent): C, 49.09; H, 5.14; N, 9.50.

NMR (DMSO-$d_6$, TMS): 1.27d (7.0 Hz), 3.01septet (7.0 Hz), 6.61d (13.9 Hz), 7.61m, 7.90m, 9.7bs, 10.0bs, 11.8bs.

EXAMPLE 40

N-(3,4-Dichlorostyrylsulfonyl)-3-methylbutyramidine treated with sodium hydroxide according to the procedure of Example 1 provides N-(3,4-DICHLOROSTYRYL)-3-METHYLBUTYRAMIDINE HYDROCHLORIDE, m.p. 218.0°–220.0° C. (corr.), in 55% analytical yield from ethyl acetate-methanol.

Analysis. Calcd. for $C_{13}H_{16}Cl_2N_2.HCl$ (percent): C, 50.75; H, 5.57; N, 9.10. Found (percent): C, 50.50; H, 5.54; N, 9.17.

NMR (MDSO-$d_6$, TMS): 0.95d (6.2 Hz), 2.10m, 2.48m, 6.58d (14.0 Hz), 7.55m, 7.97m, 10.3bs, 12.2bs.

EXAMPLE 41

N-(3,4-Dichlorostyrylsulfonyl)-2,2-dimethylpropionamidine treated with sodium hydroxide according to the procedure of Example 1 provides N-(3,4-DICHLOROSTYRYL)-2,2-DIMETHYLPROPIONAMIDE HYDROCHLORIDE, m.p. 246.5°–248.5° C. (dec.)(corr.) in 35% analytical yield, by crystallization from ethyl acetate-methanol.

Analysis. Calcd. for $C_{13}H_{16}Cl_2N_2.HCl$ (percent): C, 50.75; H, 5.57; N, 9.10. Found (percent): C, 50.65; H, 5.37; N, 9.07.

NMR (DMSO-$d_6$, TMS): 1.37s, 6.90d (13.6 Hz), 7.53m, 7.93m, 9.8bs.

EXAMPLE 42

N-(3,4-Dichlorostyrylsulfonyl)cyclopropanecarboxamidine treated with sodium hydroxide according to the procedure of Example 1 provides N-(3,4-DICHLOROSTYRYL)CYCLOPROPANECARBOXAMIDINE HYDROCHLORIDE, m.p. 214.0°–216.0° C. (corr.), in 65% analytical yield by crystallization from ethyl acetate.

EXAMPLE 43

N-(2,6-Dichlorostyrylsulfonyl)propionamidine treated with sodium hydroxide according to the procedure of Example 1 provides N-(2,6-DICHLOROSTYRYL)PROPIONAMIDINE HYDROCHLORIDE, m.p. 222°–227° C., (corr.) in 29% analytical yield by crystallization from isopropyl alcohol-isopropyl ether.

Analysis. Calcd. for $C_{11}H_{12}Cl_2N_2 \cdot HCl$ (percent): C, 47.25; H, 4.69; N, 10.02. Found (percent): C, 47.18; H, 4.74; N, 10.06.

NMR (DMSO-$d_6$, TMS): 1.28t (7.4 Hz), 2.64quartet (7.4 Hz), 6.71d (14.0 Hz), 7.44m, 9.9bs, 12.2bs.

EXAMPLE 44

N-(2,6-Dichlorostyrylsulfonyl)butyramidine treated with sodium hydroxide according to the procedure of Example 1 provides N-(2,6-DICHLOROSTYRYL)BUTYRAMIDINE HYDROCHLORIDE, m.p. 195.5°–198.5° C., (corr.) in 43% analytical yield by crystallization from isopropyl alcohol-isopropyl ether.

Analysis. Calcd. for $C_{12}H_{14}Cl_2N_2 \cdot HCl$ (percent): C, 49.09; H, 5.15; N, 9.54. Found (percent): C, 48.78; H, 5.34; N, 9.62.

NMR (DMSO-$d_6$, TMS): 0.94t (6.8 Hz), 1.71m, 2.59m, 6.69d (14.0 Hz), 7.41m, 7.47d (14.0 Hz), 9.8bs.

EXAMPLE 45

Treatment of N-(2,6-dichlorostyrylsulfonyl)-2-methylpropionamidine with sodium hydroxide according to the procedure of Example 1 provides N-(2,6-DICHLOROSTYRYL)-2-METHYLPROPIONAMIDINE HYDROCHLORIDE, m.p. 210.5°–213.5° C. (corr.), in 38% analytical yield by crystallization from ethyl acetate-methanol.

Analysis. Calcd. for $C_{12}H_{14}Cl_2N_2 \cdot HCl$ (percent): C, 49.09; H, 5.15; N, 9.54. Found (percent): C, 48.84; H, 5.19; N, 9.29.

NMR (DMSO-$d_6$, TMS): 1.30d (6.7 Hz), 3.06septet (6.7 Hz), 6.78d (14.1 Hz), 7.42m, 9.7bs, 11.9bs.

EXAMPLE 46

N-(2,6-Dichlorostyrylsulfonyl)-2,2-dimethylpropionamidine treated with sodium hydroxide according to the procedure of Example 1 provides N-(2,6-DICHLOROSTYRYL)-2,2-DIMETHYLPROPIONAMIDINE HYDROCHLORIDE, m.p. 207°–210° C. (corr.) in 48% analytical yield by crystallization from ethyl acetate-methanol.

Analysis. Calcd. for $C_{13}H_{16}Cl_2N_2 \cdot HCl$ (percent): C, 50.75; H, 5.57; N, 9.10. Found (percent): C, 50.86; H, 5.77; N, 9.01.

NMR (DMSO-$d_6$, TMS): 1.39s, 7.06d (13.8 Hz), 7.42m, 7.49d (13.8 Hz), 9.5bs.

EXAMPLE 47

N-(2,6-Dichlorostyrylsulfonyl)cyclopropanecarboxamidine treated with sodium hydroxide according to the procedure of Example 1 provides N-(2,6-DICHLOROSTYRYL)CYCLOPROPANECARBOXAMIDINE HYDROCHLORIDE, m.p. 199.5°–201.5° C. (corr.) in 49% analytical yield by crystallization from ethyl acetate-methanol.

Analysis. Calcd. for $C_{12}H_{12}Cl_2N_2 \cdot HCl$ (percent): C, 49.43; H, 4.49; N, 9.61. Found (percent): C, 49.41; H, 4.57; N, 9.54.

NMR (DMSO-$d_6$, TMS): 1.27m, 2.18m, 6.70d (14.0 Hz), 7.41m, 9.2bs, 12.0bs.

EXAMPLE 48

N-(2,6-Dichlorostyrylsulfonyl)benzamidine treated with sodium hydroxide according to the procedure of Example 1 provides N-(2,6-DICHLOROSTYRYL)BENZAMIDINE HYDROCHLORIDE, m.p. 201°–205.5° C. (corr.), in 49% analytical yield by crystallization from ethyl acetate-methanol.

Analysis. Calcd. for $C_{15}H_{12}Cl_2N_2 \cdot HCl$ (percent): C, 54.99; H, 4.00; N, 8.55. Found (percent): C, 54.93; H, 4.01; N, 8.40.

NMR (DMSO-$d_6$, TMS): 6.98d (13.8 Hz), 7.64m, 10.0bs.

EXAMPLE 49

N-(2,6-Dichlorostyrylsulfonyl)phenylacetamidine treated with sodium hydroxide according to the procedure of Example 1 provides N-(2,6-DICHLOROSTYRYL)PHENYLACETAMIDINE HYDROCHLORIDE, m.p. 207.5°–210.5° C. in 44% analytical yield by crystallization from ethyl acetate-methanol.

Analysis. Calcd. for $C_{16}H_{14}Cl_2N_2 \cdot HCl$ (percent): C, 56.25; H, 4.43; N, 8.20. Found (percent): C, 55.97; H, 4.46; N, 8.15.

NMR (DMSO-$d_6$, TMS): 3.99septet, 6.77d (14.2 Hz), 7.45m, 10.0bs.

EXAMPLE 50

N-(2,4-Dichlorostyrylsulfonyl)acetamidine treated with sodium hydroxide according to the procedure of Example 1 provides N-(2,4-DICHLOROSTYRYL)ACETAMIDINE HYDROCHLORIDE, m.p. 228.0°–232.0° C. (corr.) in 50% analytical yield.

Analysis. Calcd. for $C_{10}H_{10}Cl_2N_2 \cdot HCl$ (percent): C, 45.23; H, 4.18; N, 10.55. Found (percent): C, 45.20; H, 4.17; N, 10.44.

NMR (DMSO-$d_6$, TMS): 2.32s, 6.81d (14.0 Hz), 7.41m, 7.91d (8.1 Hz), 8.03d (14.0 Hz), 10.0bs.

EXAMPLE 51

N-(2-Chlorostyrylsulfonyl)acetamidine treated with sodium hydroxide according to the procedure of Example 1 provides N-(2-CHLOROSTYRYL)ACETAMIDINE HYDROCHLORIDE HYDRATE, m.p. 193° C. (corr.).

Analysis. Calcd. for $C_{10}H_{11}ClN_2 \cdot HCl \cdot H_2O$: C, 49.64; H, 5.50; N, 11.57; $H_2O$; 4.46. Found: C, 49.58; H, 5.49; N, 11.51; $H_2O$, 4.42.

EXAMPLE 52

The following 3,4-dichlorostyrylamidine products of Formula I are obtained by treating the enumerated styrylsulfonylamidine precursors with sodium hydroxide in dimethylsulfoxide according to the procedure of Example 1:

(a) N-(3,4-DICHLOROSTYRYL)-3-METHYLBUTYRAMIDE from N-(3,4-dichlorostyrylsulfonyl)-3-methylbutyramidine, (b) N-(3,4-DICHLOROSTYRYL)-2,2-DIMETHYL-PROPIONAMIDINE from N-(3,4-dichlorostyrylsulfonyl)-2,2-dimethylpropionamidine.

(c) N-(3,4-DICHLOROSTYRYL)HEXANAMIDINE from N-(3,4-dichlorostyrylsulfonyl)hexanamidine, (d) N-(3,4-DICHLOROSTYRYL)HEPTANAMIDINE from N-(3,4-dichlorostyrylsulfonyl)heptanamidine, (e) N-(3,4-DICHLOROSTYRYL)-2-METHYLHEXANAMIDINE from N-(3,4-dichlorostyrylsulfonyl)-2-methylhexanamidine, (f) N-(3,4-DICHLOROSTYRYL)-2,2-DIMETHYLBUTYRAMIDINE from N-(3,4-dichlorostyrylsulfonyl)-2,2-dimethylbutyramidine, (g) N-(3,4-DICHLOROSTYRYL)CYCLOBUTANECARBOXAMIDINE from N-(3,4-dichlorostyrylsulfonyl)cyclobutanecarboxamidine, (h) N-(3,4-DICHLOROSTYRYL)CYCLOPENTANECARBOXAMIDINE from N-(3,4-dichlorostyrylsulfonyl)cyclopentanecarboxamidine, (i) N-(3,4-DICHLOROSTYRYL)CYCLOHEXANECARBOXAMIDINE from N-(3,4-dichlorostyrylsulfonyl)cyclohexanecarboxamidine, (j) N-METHYL-N-(3,4-DICHLOROSTYRYL)ACETAMIDINE from N-methyl-N'-(3,4-dichlorostyrylsulfonyl)acetamidine.

An alternate method for the preparation of N-methyl-N-(3,4-dichlorostyryl)acetamidine involves the N-methylation of N-(3,4-dichlorostyryl)acetamidine (9.2 g., 0.04 mole) with methyl fluorosulfonate (5.7 g., 0.05 mole) in 50 ml. of dichloromethane. The reaction mixture is basified with 10% sodium hydroxide and the organic layer separated, dried, and concentrated to provide the free base which is taken up in acetone and acidified with ethanolic hydrogen chloride. The product thus obtained is crystallized from ethanol-isopropyl ether to afford analytically pure N-METHYL-N-(3,4-DICHLOROSTYRYL)ACETAMIDINE HYDROCHLORIDE, m.p. 238°–239° C., (dec.)(corr.).

Analysis. Found (percent): C, 47.24; H, 4.77; N, 10.03.

NMR (DMSO-$d_6$, TMS): 2.58s, 3.39s, 6.70d (14.0 Hz), 7.80m, 10.2bs.

EXAMPLE 53

The following styrylamidine products of Formula I are obtained by treating the enumerated styrylsulfonylamidine precursor with sodium hydroxide in dimethylsulfoxide according to the procedure of Example 1:

(a) N-(2-CHLORO-6-METHYLSTYRYL)ACETAMIDINE from N-(2-Chloro-6-methylstyrylsulfonyl)acetamidine, (b) N-(4-METHYLSULFONYLSTYRYL)ACETAMIDINE from N-(4-methylsulfonylstyrylsulfonyl)acetamidine, (c) N-(2,6-DITRIFLUOROMETHYLSTYRYL)ACETAMIDINE from N-(2,6-ditrifluoromethylstyrylsulfonyl)acetamidine, (d) N-(2-TRIFLUOROMETHYLSTYRYL)ACETAMIDINE from N-(2-trifluoromethylstyrylsulfonyl)acetamidine, (e) N-(2,3,6-TRICHLOROSTYRYL)ACETAMIDINE from N-(2,3,6-trichlorostyrylsulfonyl)acetamidine, (f) N-CYCLOPROPYL-N-(2,6-DICHLOROSTYRYL)ACETAMIDINE from N-cyclopropyl-N'-(2,6-dichlorostyrylsulfonyl)acetamidine.

(g) N-CYCLOPROPYL-N-(3,4-DICHLOROSTYRYL)ACETAMIDINE from N-cyclopropyl-N'-(3,4-dichlorostyrylsulfonyl)acetamidine.

(h) N-METHYL-N-(2,6-DICHLOROSTYRYL)ACETAMIDINE from N-methyl-N'-(2,6-dichlorostyrylsulfonyl)acetamidine.

Methylation of N-(2,6-dichlorostyryl)acetamidine with methyl fluorosulfonate according to the method of Example 52(j) provides an alternate method for preparing N-methyl-N-(2,6-dichlorostyryl)acetamidine. N-Methyl-N-(2,6-dichlorostyryl)acetamidine hydrochloride is obtained analytically pure by crystallization from absolute ethanol-isopropyl ether and has a melting point of 215°–217° C. (dec.)(corr.).

Analysis. Found (percent): C, 47.15; H, 4.67; N, 9.91.

NMR (DMSO-$d_6$, TMS): 2.55s, 3.47s, 6.55d (14.1 Hz), 7.60m, 10.5bs.

EXAMPLE 54

Reaction of the styrylsulfonyl chlorides and amidines enumerated below according to the procedures set forth in Example 29 provides the following styrylsulfonylamidine precursors of styrylamidine products of the instant invention.

(a) N-(2,6-DICHLOROSTYRYLSULFONYL)BENZAMIDINE, m.p. 154°–157° C. (corr.), from 2,6-dichlorostyrylsulfonyl chloride and benzamidine.

Analysis. Calcd. for $C_{15}H_{12}Cl_2N_2O_2S$ (percent): C, 50.72; H, 3.41; N, 7.88. Found (percent): C, 50.68; H, 3.58; N, 7.72.

(b) N-(2,6-DICHLOROSTYRYLSULFONLY)PHENYLACETAMIDINE, m.p. 183°–185° C. (corr.), from 2,6-dichlorosulfonyl chloride and phenylacetamidine.

Analysis. Calcd. for $C_{16}H_{14}Cl_2N_2O_2S$ (percent): C, 52.64; H, 3.82; N, 7.59. Found (percent); C, 51.91; H, 3.91; N, 7.45.

(c) N-(2,6-DICHLOROSTYRYLSULFONYL)-2-METHYLPROPIONAMIDINE, m.p. 146°–148° C., from 2,6-dichlorostyrylsulfonyl chloride and 2-methylpropionamidine.

Analysis. Calcd. for $C_{12}H_{14}Cl_2N_2O_2S$ (percent): C, 44.87; H, 4.39; N, 8.72. Found (percent): C, 44.88; H, 4.38; N, 8.77.

(d) N-(2,6-DICHLOROSTYRYLSULFONYL)BUTYRAMIDINE, m.p. 155°–157° C., from 2,6-dichlorostyrylsulfonyl chloride and butyramidine.

Analysis. Calcd. for $C_{12}H_{14}Cl_2N_2O_2S$ (percent): C, 44.87; H, 4.39; N, 8.72. Found (percent): C, 44.77; H, 4.37; N, 8.78.

(e) N-(2,6-DICHLOROSTYRYLSULFONYL)-2,2-DIMETHYLPROPIONAMIDINE, m.p. 160°–162° C., from 2,6-dichlorostyrylsulfonyl chloride and 2,2-dimethylpropionamidine.

Analysis. Calcd. for $C_{13}H_{16}Cl_2N_2O_2S$ (percent): C, 46.57; H, 4.81; N, 8.35. Found (percent): C, 46.37; H, 4.79; N, 8.23.

(f) N-(2,6-DICHLOROSTYRYLSULFONYL)CYCLOPROPANECARBOXAMIDINE, m.p. 176°–179° C., from 2,6-dichlorostyrylsulfonyl chloride and cyclopropanecarboxamidine.

(g) N-(2,6-DICHLOROSTYRYLSULFONYL)PROPIONAMIDINE from 2,6-dichlorostyrylsulfonyl chloride and propionamidine.

(h) N-(3,4-DICHLOROSTYRYLSULFONYL)-2-METHYLPROPIONAMIDINE, m.p. 177°–180° C., from 3,4-dichlorostyrylsulfonyl chloride and 2-methylpropionamidine.

(i) N-(3,4-DICHLOROSTYRYLSULFONYL)-BUTYRAMIDINE, m.p. 140°–145° C., from 3,4-dichlorostyrylsulfonyl chloride and butyramidine.

(j) N-(3,4-DICHLOROSTYRYLSULFONYL)-2,2-DIMETHYLPROPIONAMIDINE, m.p. 135°–137° C., from 3,4-dichlorostyrylsulfonyl chloride and 2,2-dimethylpropionamidine.

(k) N-(3,4-DICHLOROSTYRYLSULFONYL)CYCLOPROPANECARBOXAMIDINE, m.p. 208°–213° C., from 3,4-dichlorostyrylsulfonyl chloride and cyclopropanecarboxamidine.

(l) N-(3,4-DICHLOROSTYRYLSULFONYL)-PROPIONAMIDINE, m.p. 194°–197° C., from 3,4-dichlorostyrylsulfonyl chloride and propionamidine.

(m) N-(3,4-DICHLOROSTYRYLSULFONYL)-PENTANEAMIDINE, m.p. 135°–140° C., from 3,4-dichlorostyrylsulfonyl chloride and pentanamidine.

(n) N-(3,4-DICHLOROSTYRYLSULFONYL)-3-METHYLBUTYRAMIDINE, m.p. 184°–186° C., from 3,4-dichlorostyrylsulfonyl chloride and 3-methylbutyramidine.

(o) N-(2,4-DICHLOROSTYRYLSULFONYL)ACETAMIDINE, m.p. 216°–219° C., from 2,4-dichlorostyrylsulfonyl chloride and acetamidine.

(p) N-(2-CHLOROSTYRYLSULFONYL)ACETAMIDINE, m.p. 161°–165° C. from 2-chlorostyrylsulfonyl chloride and acetamidine.

(q) N-(2-CHLORO-6-METHYLSTYRYLSULFONYL)ACETAMIDINE from 2-chloro-6-methylstyrylsulfonyl chloride and acetamidine.

(r) N-(2,3,6-TRICHLOROSTYRYLSULFONYL)ACETAMIDINE from 2,3,6-trichlorostyrylsulfonyl chloride and acetamidine.

EXAMPLE 55

Reaction of Cyclopyropylamine with N-(2,6-dichlorostyrylsulfonyl)chloroacetimidate according to the procedure of Example 32(b) affords N-cyclopropyl-N'-(2,6-dichlorostyrylsulfonyl) acetamidine, m.p. 121°–124° C. when crystallized from benzene.

The corresponding N-cyclopropyl-N'-(3,4-dichlorostyrylsulfonyl)acetamidine is obtained in a similar fashion by reaction of cyclopropylamine with N-(3,4-dichlorostyrylsulfonyl)chloroacetimidate.

EXAMPLE 56

Oral Administration of Representative StyrylAmidines

The styrylamidine is orally administered to each rabbit in a group of 2-6 rabbits at a single dose of 25 mg./kg. body weight. A 8 ml. portion of blood is drawn just prior to dosing in order to obtain a control value and at various time periods thereafter. Platelet rich plasma is prepared from each blood sample by centrifugation at 200 times gravity for 10 min. at room temperature. Samples (0.5 ml.) of platelet rich plasma are tested for their ability to aggregate with either collagen or adenosine-5'-diphosphate added as specified in the modification of Born and O'Brien method which has been fully described hereinbefore. The results shown below indicate the inhibition of blood platelet aggregation induced by the lowest amount of collagen giving maximal aggregation or 0.25–1.0 microgram adenosine-5'-diphosphate for representative amidines.

| Styrylamidine | Time (hrs.) | % Inhibition of Blood Platelet Aggregation Induced by: | |
|---|---|---|---|
| | | ADP | Collagen |
| N-(3,4-Dichlorostyryl)-acetamidine hydrochloride | 1 | 50 | 67 |
| | 2 | 52 | 50 |
| | 4 | 67 | 85 |
| | 6 | 55 | 55 |
| | 24 | 0 | 0 |
| N-(3,4-Dichlorostyryl)-butyramidine hydrochloride | 1 | 18 | 30 |
| | 2 | 67 | 92 |
| | 4 | 37 | 32 |
| | 6 | 30 | 45 |
| | 24 | 0 | 0 |
| N-(3,4-Dichlorostyryl)-2,2-dimethylpropionamidine | 1 | 60 | 78 |
| | 2 | 25 | 80 |
| | 4 | 67 | 95 |
| | 6 | 87 | 95 |
| | 24 | 0 | 0 |
| N-(3,4-Dichlorostyryl)-cyclopropanecarboxamidine hydrochloride | 1 | 60 | 65 |
| | 2 | 55 | 85 |
| | 4 | 90 | 97 |
| | 6 | 75 | 87 |
| | 24 | 5 | 15 |
| N-(3,4-Dichlorostyryl)-benzamidine hydrochloride | 0.5 | 61 | 73 |
| | 1 | — | — |
| | 2 | 54 | 65 |
| | 4 | 30 | 26 |
| | 6 | 22 | 3 |
| | 24 | 0 | 0 |

What is claimed is:

1. A compound selected from the group consisting of styrylsulfonylamidines having the formula

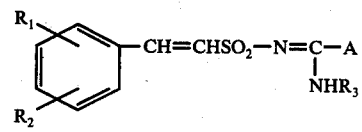

wherein
R$_1$ is selected from lower alkyl of 1 to 4 carbon atoms inclusive, hydrogen, nitro, amino, halogen, cyclohexyl, carbamoyl, lower alkylsulfonyl from 1 to 4 carbon atoms inclusive, sulfamoyl or lower alkanoylamido of from 2 to 4 carbon atoms inclusive;
R$_2$ is selected from hydrogen or halogen with the proviso that when R$_1$ is halogen R$_2$ can represent up to two additional halogen;
R$_3$ is hydrogen, cyclopropyl or lower alkyl of 1 to 4 carbon atoms inclusive;
A is selected from lower alkyl of from 1 to 8 carbon atoms inclusive, di(lower)alkylaminophenyl, phenyl, benzyl, β-naphthyl, styryl, phenylbutadienyl, cycloalkyl of 3 to 6 carbon atoms inclusive, or a substituted phenyl radical represented by the symbol

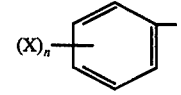

wherein
X is selected from (lower) alkoxy from 1 to 4 carbon atoms inclusive, halogen, nitro, amino, lower alkanoylamido of from 2 to 4 carbon atoms inclusive, and
n represents the integer 1 or 2.

2. The compound according to claim 1 consisting of N-(styrylsulfonyl)acetamidine.

3. The compound according to claim 1 consisting of N-(styrylsulfonyl)benzamidine.

4. The compound according to claim 1 consisting of N-(4-nitrostyrylsulfonyl)acetamidine.

5. The compound according to claim 1 consisting of N-[(3,4-dichlorostyryl)sulfonyl]acetamidine.

6. The compound according to claim 1 consisting of N-[(3,4-dichlorostyryl)sulfonyl]cyclopropanecarboxamidine.

7. The compound according to claim 1 consisting of N-[(2,6-dichlorostyryl)sulfonyl]acetamidine.

8. The compound according to claim 1 consisting of N-[(2,6-dichlorostyryl)sulfonyl]propionamidine.

9. The compound according to claim 1 consisting of N-[(2,6-dichlorostyryl)sulfonyl]cyclopropanecarboxamidine.

10. The compound according to claim 1 consisting of N-(4-nitrosytyrlsulfonyl)-4-aminobenzamidine.

11. The compound according to claim 1 consisting of N-[(4-chlorostyryl)sulfonyl]acetamidine.

12. The compound according to claim 1 consisting of N-[(3,4-dichlorostyryl)sulfonyl]phenylacetamidine.

13. The compound according to claim 1 consisting of N-[(3,4-dichlorostyryl)sulfonyl]benzamidine.

14. The compound according to claim 1 consisting of N-(2-nitrostyrylsulfonyl)acetamidine.

15. The compound according to claim 1 consisting of N-(4-nitrostyrylsulfonyl)benzamidine.

16. The compound according to claim 1 consisting of N-(4-nitrostyrylsulfonyl)-4-nitrobenzamidine.

17. The compound according to claim 1 consisting of N-(4-nitrostyrylsulfonyl)-3-nitrobenzamidine.

18. The compound according to claim 1 consisting of N-(4-nitrostyrylsulfonyl)-3-aminobenzamidine.

19. The compound according to claim 1 consisting of N-(4-nitrostyrylsulfonyl)-4-dimethylaminobenzamidine.

20. The compound according to claim 1 consisting of N-(4-nitrostyrylsulfonyl)cinnamidine.

21. The compound according to claim 1 consisting of N-(4-nitrostyrylsulfonyl)-β-naphthamidine.

22. The compound according to claim 1 consisting of N-(3,4-dichlorostyrylsulfonyl)-3,4-dimethoxybenzamidine.

23. The compound according to claim 1 consisting of N-(3-bromo-4-cyclohexylstyrylsulfonyl)acetamidine.

24. The compound according to claim 1 consisting of N-methyl-N'-(4-nitrostyrylsulfonyl)benzamidine.

25. The compound according to claim 1 consisting of N-(2,6-dichlorostyrylsulfonyl)benzamidine.

26. The compound according to claim 1 consisting of N-(2,6-dichlorostyrylsulfonyl)phenylacetamidine.

27. The compound according to claim 1 consisting of N-(2,6-dichlorostyrylsulfonyl)-2-methylpropionamidine.

28. The compound according to claim 1 consisting of N-(2,6-dichlorostyrylsulfonyl)butyramidine.

29. The compound according to claim 1 consisting of N-(2,6-dichlorostyrylsulfonyl)-2,2-dimethylpropionamidine.

30. The compound according to claim 1 consisting of N-(3,4-dichlorostyrylsulfonyl)-2-methylpropionamidine.

31. The compound according to claim 1 consisting of N-(3,4-dichlorostyrylsulfonyl)butyramidine.

32. The compound according to claim 1 consisting of N-(3,4-dichlorostyrylsulfonyl)-2,2-dimethylpropionamidine.

33. The compound according to claim 1 consisting of N-(3,4-dichlorostyrylsulfonyl)propionamidine.

34. The compound according to claim 1 consisting of N-(3,4-dichlorostyrylsulfonyl)pentaneamidine.

35. The compound according to claim 1 consisting of N-(3,4-dichlorostyrylsulfonyl)-3-methylbutyramidine.

36. The compound according to claim 1 consisting of N-(2,4-dichlorostyrylsulfonyl)acetamidine.

37. The compound according to claim 1 consisting of N-(2-chlorostyrylsulfonyl)acetamidine.

38. The compound according to claim 1 consisting of N-(2-chloro-6-methylstyrylsulfonyl)acetamidine.

39. The compound according to claim 1 consisting of N-(2,3,6-trichlorostyrylsulfonyl)acetamidine.

* * * * *